US006737547B1

(12) United States Patent
Sklarz et al.

(10) Patent No.: US 6,737,547 B1
(45) Date of Patent: May 18, 2004

(54) COMPOSITIONS CONTAINING AND METHODS OF USING N-ACYL-1H-AMINOINDENES

(75) Inventors: Benjamin Sklarz, Petach-Tikva (IL); Sasson Cohen, Tel-Aviv (IL); Tzipora Speiser, Tel-Aviv (IL); Rachel Nachman, Tel-Aviv (IL)

(73) Assignee: Teva Pharmaceutical Industries, Ltd. (IL)

( * ) Notice: Subject to any disclaimer, the term of this patent is extended or adjusted under 35 U.S.C. 154(b) by 0 days.

(21) Appl. No.: 09/397,633

(22) Filed: Sep. 15, 1999

Related U.S. Application Data

(60) Provisional application No. 60/114,397, filed on Dec. 31, 1998.

(51) Int. Cl.[7] ............... C07C 233/05; A61K 31/16
(52) U.S. Cl. ............... 564/215; 564/222; 560/27; 560/28; 514/480; 514/481; 514/625; 514/629
(58) Field of Search ............... 514/480, 481, 514/615, 629; 560/27, 28; 564/215, 222

(56) References Cited

U.S. PATENT DOCUMENTS

| 2,573,645 A | 10/1951 | Kerwin et al. |
|---|---|---|
| 2,916,490 A | 12/1959 | Schenck et al. |
| 2,982,783 A | 5/1961 | Schenck et al. |
| 3,060,091 A | 10/1962 | Witkin |
| 3,123,642 A | 3/1964 | Temple et al. |
| 3,178,478 A | 4/1965 | Huebner et al. |
| 3,201,470 A | 8/1965 | Huebner et al. |
| 3,253,037 A | 5/1966 | Huebner et al. |
| 3,308,157 A | 3/1967 | Robertson et al. |
| 3,513,244 A | 5/1970 | Gittos et al. |
| 3,637,740 A | 1/1972 | Sarges |
| 3,704,323 A | 11/1972 | Krapcho |
| 3,709,996 A | 1/1973 | Gittos et al. |
| 3,751,420 A | 8/1973 | Hauck et al. |
| 3,804,898 A | 4/1974 | Panneman |
| 3,886,168 A | 5/1975 | Himmele et al. |
| 3,991,207 A | 11/1976 | Sarges et al. |
| 4,029,731 A | 6/1977 | Sarges |

(List continued on next page.)

FOREIGN PATENT DOCUMENTS

| EP | 0436492 A2 | 10/1991 |
|---|---|---|
| GB | 0852735 | 11/1960 |
| GB | 1003686 A | 9/1965 |

(List continued on next page.)

OTHER PUBLICATIONS

Ruschig et al., "Preparation of 17α–hydroxy–20–keto Steroids from 17(20)–en–20–acetamino Steroids", *Chem. Ber.* (1955) 88(6):883–894, including an English language abstract (Exhibit 2).

(List continued on next page.)

*Primary Examiner*—Shailendra Kumar
(74) *Attorney, Agent, or Firm*—John P. White; Cooper & Dunham LLP

(57) ABSTRACT

The present invention provides novel aminoindenes having the structure:

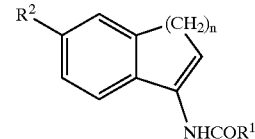

wherein n is 1 or 2, $R^1$ is hydrogen, linear or branched chain $C_1$–$C_8$ alkyl or linear or branched chain $C_1$–$C_8$ alkoxy and $R^2$ is hydrogen or a halogen. Such compounds may be used to treat neurodegenerative conditions such as Alzheimer's disease, head trauma, stroke, hypoxia, anoxia, epilepsy, convulsions, seizures.

35 Claims, 12 Drawing Sheets

U.S. PATENT DOCUMENTS

| | | |
|---|---|---|
| 4,096,173 A | 6/1978 | Molloy |
| 4,128,666 A | 12/1978 | Bondinell et al. |
| 4,132,737 A | 1/1979 | Molloy |
| 4,134,997 A | 1/1979 | Cannon et al. |
| 4,172,093 A | 10/1979 | Göransson-Dahlander et al. |
| 4,632,939 A | 12/1986 | Beedle et al. |
| 4,638,001 A | 1/1987 | Kuhla et al. |
| 4,788,130 A | 11/1988 | Oshiro et al. |
| 4,792,628 A | 12/1988 | Oshiro et al. |
| 4,826,875 A | 5/1989 | Chiesi |
| 4,833,273 A | 5/1989 | Goel et al. |
| 4,873,241 A | 10/1989 | Napier et al. |
| 5,011,995 A | 4/1991 | Pugin et al. |
| 5,071,875 A | 12/1991 | Horn et al. |
| 5,118,704 A | 6/1992 | Minaskanian et al. |
| 5,134,147 A | 7/1992 | Peglion et al. |
| 5,153,225 A | 10/1992 | Schohe et al. |
| 5,189,045 A | 2/1993 | Peglion et al. |
| 5,196,583 A | 3/1993 | Yamada et al. |
| 5,225,596 A | 7/1993 | Carlsson et al. |
| 5,242,919 A | 9/1993 | Oshiro et al. |
| 5,286,747 A | 2/1994 | Arvidsson et al. |
| 5,378,729 A | 1/1995 | Kohn et al. |
| 5,387,612 A | 2/1995 | Youdim et al. |
| 5,389,687 A | 2/1995 | Schaus et al. |
| 5,401,758 A | 3/1995 | Atwal et al. |
| 5,453,446 A | 9/1995 | Youdim et al. |
| 5,457,133 A | 10/1995 | Youdim et al. |
| 5,516,943 A | 5/1996 | Gao et al. |
| 5,519,061 A | 5/1996 | Youdim et al. |
| 5,532,415 A | 7/1996 | Youdim et al. |
| 5,569,669 A | 10/1996 | Guillaumet et al. |
| 5,646,188 A | 7/1997 | Gilad et al. |
| 5,654,301 A | 8/1997 | Kohn et al. |
| 5,708,018 A | 1/1998 | Haadsma-Svensson et al. |
| 5,877,218 A | 3/1999 | Herzig et al. |
| 5,914,349 A | 6/1999 | Cohen et al. |

FOREIGN PATENT DOCUMENTS

| | | |
|---|---|---|
| WO | WO9504027 A1 | 2/1995 |
| WO | WO9511016 A1 | 4/1995 |
| WO | WO9518617 A1 | 7/1995 |

OTHER PUBLICATIONS

Armstrong et al., "Acylation Effects on Chiral Recognition of Racemic Amines and Alcohols by New Polar and Non-Polar Cyclodextrin Derivative Gas Chromatographic Phases", *J. Chromatography* (1990) 502: 154–159 (Exhibit 61).

Askin et al., "Highly Diastereoselective Alkylations of Chiral Amide Enolates: New Routes to Hydroxyethylene Dipeptide Isostere Inhibitors of HIV–1 Protease", *J. Org. Chem.* (1992) 57(10): 2771–2773 (Exhibit 62).

Baker et al., "Synthesis of Decahydrocyclopentacylco–octene Derivatives via Intramolecular—Photocycloaddition of $\Delta^{\alpha,\beta}$ Butenolides and Reductive Cleavage", *J. Chem. Soc. Chem. Comm.* (1980) 23: 1011–1012 (Exhibit 63).

Barton et al., "Reductive Formylation of Oximes; An Approach to the Synthesis of Vinyl Isonitriles", *Tetrahedron Letters* (1988) 29(27): 3343–3346 (Exhibit 64).

Boar et al., "A Simple Synthesis of Enamides from Ketoximes", *J. Chem. Soc. Perkins I* (1975) 1237–1241 (Exhibit 65).

Brettle et al., "Synthesis of Enamides", *J. Chem. Soc. Perkin Trans. I*, (1988) 2185–2193 (Exhibit 66).

Burk et al., "A Three–Step Procedure for Asymmetric Catalytic Reductive Amidation of Ketones", *J. Org. Chem.* (1998), 63, 6084–6085 (Exhibit 67).

Drefahl et al., "Amino Alcohols. I. Cis– and Trans–DL–1–amino–2–hydroxytetrahydronaphthalene and Cis– and Trans–DL–1–amino–2–hydroxyindan", *Chem. Abstracts* (1958) 52: 16417f (Exhibit 68).

Drefahl et al., "Amino Alcohols. X. Addition of Iodine Isocyanate to Unsymmetrical Olefins", *Chem. Abstracts* (1960) 54: 13078f (Exhibit 69).

Finberg and Youdim, "Modification of Blood Pressure and Nictitating Membrane Response to Sympathetic Amines by Selective Monoamine Oxidase Inhibitors, Types A and B, in the Cat", *Brit. J. Pharmacol.* (1985) 85(2): 541–546 (Exhibit 70).

Fuller et al., "Inhibition in vitro of Norepinephrine N–methyltransferase by 2–Aminotetralins, Analogs of Phenylethylamines with Rigid Conformation", *Biochem. Pharmacol.*, (1976) 26: 446–447 (Exhibit 71).

Ghislandi et al., "Scissione Ottica E Configurazione Dell' 1–Aminobenzociclobutene E Dell' 1–Aminoindano", *Boll. Chim. Farm.* (1976) 115: 489–500 (Exhibit 72).

Heikkila et al., "Prevention of MPTP–Induced Neurotoxicity by AGN–1133 and AGN–1135, Selective Inhibitors of Monoamine Oxidase–B", *Eur. J. Pharmacol.* (1985) 116: 313–317 (Exhibit 73).

Horn et al., "Steric Requirements for Catecholamine Uptake by Rat Brain Synaptosomes: Studies with Rigid Analogs of Amphetamine", *J. Pharmacol. Exp. Ther.* (1972) 180: 523–530 (Exhibit 74).

Huebner, "1–(N–Methyl–N–propargylamino)indans and Related Compounds", *Chem. Abstracts.* (1964); 61:3046a (Exhibit 75.

Kabins et al., "Potential Applications for Monoamine Oxidase B Inhibitors", *Dementia* (1990) 1: 323–348 (Exhibit 76).

Kametani et al., "Studies on the Syntheses of Heterocyclic Compounds. CLIX. The Reaction of 2–Nitro–1–indanone Oxime with Formalin and Hydrochloric Acid", *Chem. Pharm. Bull.* (1966) 14(12): 1408–1413 (Exhibit 77).

Laso et al., "A New Selective Reduction of Nitroalkenes into Enamides", *Tetrahedron Letters* (1996) 37(10): 1605–1608 (Exhibit 78).

Martin et al., "Potential Anti–Parkinson Drugs Designed by Receptor Mapping", *J. Med. Chem.* (1973) 16(2): 147–150 (Exhibit 79).

Martin et al., "Discriminant Analysis of the Relationship Between Physical Properties and the Inhibition of Monoamine Oxidase by Aminotetralins and Aminoindans", *J. Med. Chem.* (1974) 17(4): 409–413 (Exhibit 80).

Mouna et al., "Enantioselective Acetylation of Primary Amines by *Cylindrocarpon Radicicola*", *Bioorg. & Med. Chem. Letters*, (1993) 3(4): 681–684 (Exhibit 81).

Nakanishi et al., "Preparation of Enamides via Reductive Acylation of N–Acetoxyimino Compounds by Use of $Fe_3(CO)_{12}$" *Chemistry Letters* (1987) 2167–2168 (Exhibit 82).

Oshiro et al., "Novel Cerebroprotective Agents with Central Nervous System Stimulating Activity. 1. Synthesis and Pharmacology of 1–Amino–7–hydroxyindan Derivatives", *J. Med. Che.* (1991) 34(7): 2004–2013 (Exhibit 83).

Riederer and Youdim, "Monoamine Oxidase Activity and Monoamine Metabolism in Brains of Parkinson's Patients Treated with l–Deprenyl", *J. Neurochem.* (1986) 46(5): 1359–1365 (Exhibit 84).

Singh et al., "Antimalarials. 7–Chloro–4–(substituted amino)quinolines", *J. Med. Chem.* (1971) 14(4): 283–286 (Exhibit 85).

Tekes et al., "Effect of MAO Inhibitors on the Uptake and Metabolism of Dopamine in Rat and Human Brain", *Pol. J. Pharmacol. Pharm.* (1988) 40: 653–658 (Exhibit 86).

Top et al., "N–Alkylation of Nitriles with Tricarbonylchromium Complexes of Benzyl and Related Alcohols as Synthetic Intermediates. Futher Development of the Ritter Reactions", *J.C.S. Chem. Comm.* (1979) 224–225 (Exhibit 87).

Youdim et al., "Monamine Oxidase" in *Handbook of Experimental Pharmacology*, v. 90/I.
(Trendelenburg and Weiner, eds., Springer–Verlag, London: 1988) Chpt. 3, 119–192 (Exhibit 88).

Zheng et al., "Asymmetric Synthesis of α–Amino Acid Derivatives via an Electrophilic Amination of Chiral Amide Cuprates with Li t–Butyl–N–Tosyloxycarbamate", *Tetrahedron Letters* (1997) 38(16): 2817–2820 (Exhibit 89).

Zhu et al., "Asymmetric Rh–Catalyzed Hydrogenation of Enamides with a Chiral 1,4–Bisphosphine Bearing Diphenylphosphino Groups", *J. Org. Chem.* (1998) 63: 9590–9593 (Exhibit 90).

*The Merck Index* (Windholz et al., eds., Merck & Co., Inc., Rahway, NJ, 10th ed., 1983) 149, 248–249 (Exhibit 91).

*The Merck Manual of Diagnosis and Therapy*, (Berkow et al., eds., Merck Sharp & Dohme Research Laboratories, 15$^{th}$ ed., 1987) 1030–1033 (Exhibit 92) 1054–1055 (Exhibit 93).

The Parkinson Study Group, "Effect of Deprenyl on the Progression of Disability in Early Parkinson's Disease" *New Eng. J. Med.* (1989) 321(20): 1364–1371 (Exhibit 94) and.

The Parkinson Study Group, "Effects of Tocopherol and Deprenyl on the Progression of Disability in Early Parkinson's Disease" *New Eng. J. Med.* (1993) 328(3): 176–183 (Exhibit 95).

1

2

2a

3

4

5

6

7

8

9

10

11

ROCO.O.COOR

12

13

COMPOSITIONS CONTAINING AND METHODS OF USING N-ACYL-1H-AMINOINDENES

This application claims benefit of U.S. Provisional Application No. 60/114,397, filed Dec. 31, 1998, the contents of which are hereby incorporated by reference into this application.

Throughout this application, various references are identified by authors and full citation. Disclosure of these publications in their entireties are hereby incorporated by reference into this application to more fully describe the state of the art to which this invention pertains.

BACKGROUND OF THE INVENTION

The present invention relates to novel aminoindene derivatives, their preparation and their use to treat neurodegenerative conditions such as Alzheimer's disease, idiopathic-, accident-, and drug-induced seizures, and to treat acute neurological traumatic disorders such as head trauma, stroke, hypoxia/anoxia. More specifically, the invention describes aminoindene derivatives of structure 1, wherein n is 1 or 2, $R^1$ is hydrogen or lower alkyl or lower alkoxy and $R^2$ is hydrogen or a halogen, having useful neuroprotective and anti-convulsant properties. These compounds will also be useful as adjunct therapy in the above conditions.

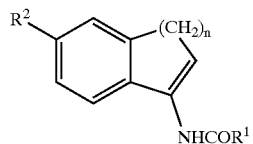

The relevant art reveals several aminoindans. See for example, Youdim, et al., (U.S. Pat. No. 5,599,991), Guillaumet et al., (U.S. Pat. No. 5,569,669), and Oshiro et al., (U.S. Pat. No. 4,788,130). Cohen, et al., International Application published under PCT, Publication No. WO 95/18617, disclosed that 1-aminoindan derivatives have anticonvulsant and other activity in the central nervous system.

One such 1-aminoindan derivative, N-acetyl-1-aminoindan (structure 2), has strong anticonvulsant activity with the R-enantiomer (structure 2a) showing somewhat greater activity than the S-isomer. This result was observed in the Maximal Electroshock Model (MES) representing general and partial seizures, and in the subcutaneous pentylenetetrazol seizure threshold test (scMET) model (mice only) representing absence seizures. However, these stereoisomers afforded only modest protection against hypobaric hypoxia in mice.

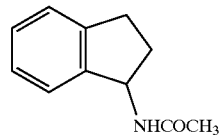

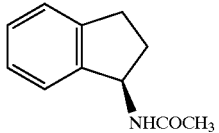

While 1-aminoindan derivatives have been well-studied, the structure and pharmacologic activity of aminoindenes remain practically unexplored. Brettle and Mosedale (J. Chem. Soc., Perkin Trans. I, 1988, 2187–95) have noted that some highly complex secondary enamides occur in nature but have not disclosed any uses of enamides.

Barton et al., Tetrahedron Letters (1988) 29: 3343–3346, prepared an analog of structure 1 where n is 2, and $R^1$ and $R^2$ are hydrogen, but solely as an intermediate in a synthesis leading to vinyl isonitriles, with no disclosure of any pharmacological studies.

Similarly, Zheng et al., Tetrahedron Letters, (1997) 38: 2817–2820, prepared an analog of structure 1 where n is 1, $R^1$ is isobutyl and $R^2$ is hydrogen. Zheng et al., obtained that compound as a minor by-product and have not explored its pharmacological activity.

In contrast to the above-described work by other investigators, the present invention discloses not only novel N-acylaminoindenes (also known as indenamides) and their synthesis, but also methods of using the N-acylaminoindenes as neuroprotectants and anticonvulsants.

As a class, the present compounds are novel, achiral with respect to the species having a five-membered ring and a more planar configuration than structure 2. One would expect that the presently disclosed aminoindene derivatives, which are achiral, would be less active than compound 2a as anticonvulsants and neuroprotectants because normally the hypothetical enzymatic or cellular active site interacting with these compounds prefers a chiral molecule. Surprisingly, the presently disclosed aminoindenes which are achiral, have shown significant anticonvulsant and neuroprotectant properties. In particular, they are anticonvulsant to about the same degree as compound 2 in the MES and scMET models described above. More significantly, they display very pronounced neuroprotective action in the hypobaric hypoxia model. They are also more effective than compound 2 in depressing response to both electrical and chemical stimulation in a guinea pig ileal preparation, and in potentiating the effect of exogenous adenosine. All this activity indicates unexpected but significant neuroprotection.

The present compounds which have been found to have neuroprotective properties are useful in neuroprotection after deprivation impact events such as trauma, stroke, and hypoxia/anoxia. The present compounds have also been found to have anticonvulsant properties which are useful in the treatment of idiopathic accident and drug-induced seizures. These compounds are also useful as adjunct therapy in the above conditions.

SUMMARY OF THE INVENTION

This invention provides compounds having the following structure:

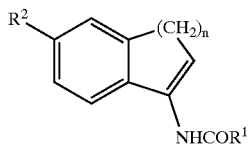

wherein n is 1 or 2, $R^1$ is hydrogen, a linear or branched chain $C_1$–$C_8$ alkyl or a linear or branched chain $C_1$–$C_8$ alkoxy and $R^2$ is hydrogen or a halogen and a pharmaceutically acceptable carrier.

This invention also provides a compound selected from the group consisting of N-acetyl-3-amino-1H-indene; N-acetyl-4-amino-1,2-dihydronaphthalene; N-formyl-3-amino-1H-indene; N-acetyl-3-amino-6-chloro-1H-indene; N-formyl-6-chloro-3-amino-1H-indene; and N-methoxycarbonyl-3-amino-1H-indene.

This invention also provides a method for treating injury or neurodamage caused by trauma, nutritive deprivation or deficiency, neurodegenerative pathology, or convulsant activity (idiopathic, drug-induced, etc.). This invention further provides a method for treating head trauma, stroke, hypoxia, anoxia, epilepsy, convulsions, seizures, or Alzheimer's disease in a subject comprising administering to the subject a therapeutically effective amount of a compound having the structural formula:

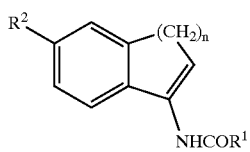

wherein n is 1 or 2, $R^1$ is hydrogen, lower alkyl or lower alkoxy and $R^2$ is hydrogen or halogen provided that where n is 1, and $R^1$ is isobutyl, $R^2$ cannot be H; and where n is 2, both $R^1$ and $R^2$ cannot be hydrogen.

This invention also provides a method of treating head trauma, stroke, hypoxia, anoxia, epilepsy, convulsions, seizures, or Alzheimer's disease in a subject comprising administering to the subject a therapeutically effective amount of a compound selected from the group consisting of: N-acetyl-3-amino-1H-indene; N-acetyl-3-amino-6-chloro-1H-indene; N-formyl-3-amino-1H-indene; N-formyl-6-chloro-3-amino-1H-indene; N-methoxycarbonyl-3-amino-1H-indene; and N-acetyl-4-amino-1,2-dihydronaphthalene.

Further, this invention provides a process for preparing a composition of claim 1, comprising detailed steps A–D:

A. reacting an oxime with a 5- or 6-membered heterocyclic amine such as pyridine or imidazole, and acetic anhydride to produce a residue;

B. agitating the residue of step (a) with sodium carbonate;

C. extracting the residue of step (b) with a suitable solvent such as an ether or an ester; and D. drying the residue of step (c) with a drying agent such as magnesium sulfate.

BRIEF DESCRIPTION OF THE FIGURES

FIG. 2 is a graphic representation of the results according to EXAMPLE 10 showing contractile response to intramural electric stimulation of the guinea pig ileal preparation in the presence of compounds 2a, 2, and 3. X-axis: drug bath concentration expressed in micromoles per liter; Y-axis: relative contraction amplitude. The drugs tested are identified in the figure legend using codes, identified as follows: (n=strips) 2a, n=6–23; 2, n=9–13; 3, n=2–17.

FIG. 3 is a logit representation of the effect of compounds 2a, 2 and 3 on the contractile response to intramural electric stimulation of the guinea-pig ileal preparation, corresponding to FIG. 2. X-axis: drug bath concentration expressed as micromoles per liter; Y-axis: log % response/(100-% response).

FIG. 4 is a graphic representation of the results according to EXAMPLE 10 showing contractile response to intramural electric stimulation of the guinea pig ileal preparation in the presence of compounds 3, 4, 5, and 6. X-axis: drug bath concentration expressed in micromoles per liter; Y-axis: relative contraction amplitude. The drugs tested are identified in the figure legend using codes, identified as follows: (n=strips) 6, n=4–6; 5, n=6–8; 3, n=2–17; 4, n=6–7.

FIG. 6 is a graphic representation of the results according to EXAMPLE 11 showing contractile response to dimethyl-phenylpiperazine chloride in the presence of rising concentrations of compounds 2a, 3, 4, 5, and 6. X-axis: drug bath concentration expressed in micromoles per liter; Y-axis: relative contraction amplitude. The drugs tested are identified in the figure legend using codes, identified as follows: (n=strips) 2a, n=2–7; 6, n=1; 5, n=1; 4, n=1; 3, n=2–4.

FIG. 8 is a graphic representation of the results according to EXAMPLE 11 showing contractile response of the guinea-pig ileal preparation to rising concentrations of dimethyl-phenylpiperazine chloride in the presence of compounds 2a or 3. X-axis: drug bath concentration expressed as micromoles per liter; Y-axis: relative contractile response.

DETAILED DESCRIPTION OF THE INVENTION

Figure 1:
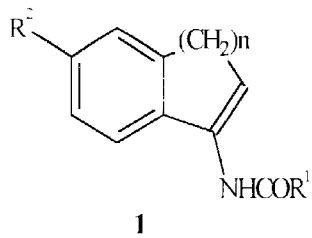
FIG. 1: The following structures are illustrated: basic structure describing the aminoindene derivatives of the invention (1); N-acetyl-1-aminoindan (2); (R)-N-acetyl-1-aminoindan (2a); N-acetyl-3-amino-1H-indene (3); N-acetyl-4-amino-1,2-dihydronapthalene (4); N-formyl-3-amino-1H-indene (5); N-acetyl-3-amino-6-chloro-1H-indene (6); N-formyl-6-chloro-3-amino-1H-indene (7); N-methoxycarbonyl-3-amino-1H-indene (8); corresponding oxime (9) used to prepare compounds derived from structure 1; 1-indanamine (10); 1-indanimine (11); dimethylpyrocarbonate (12; R=Me) or diethylpyrocarbonate (12; R=Et); N-acetyl-3-amino-6-chloroindanamide (13).
Figure 1:
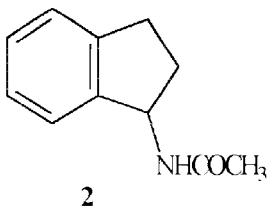
Figure 1:
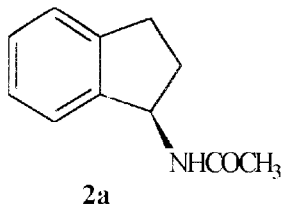
Figure 1:
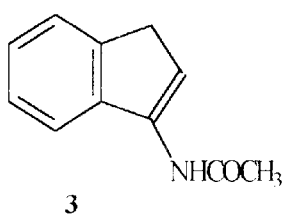
Figure 1:
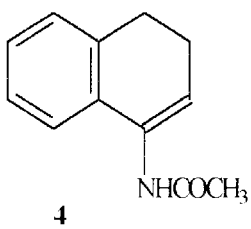
Figure 1:
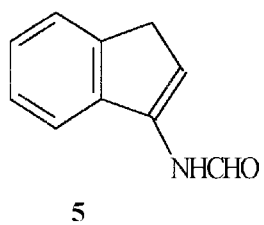
Figure 1:
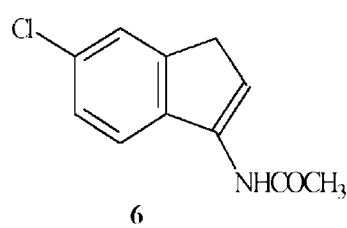
Figure 1:
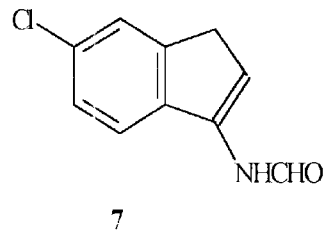
Figure 1:
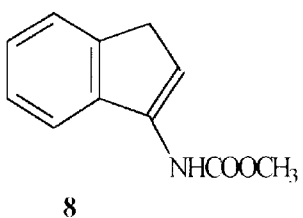
Figure 1:
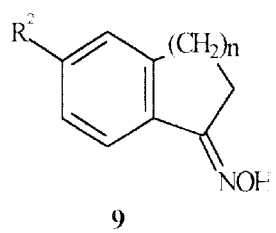
Figure 1:
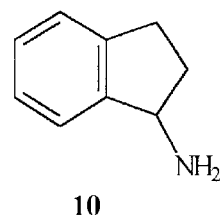
Figure 1:
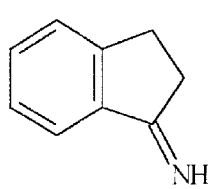
Figure 1:
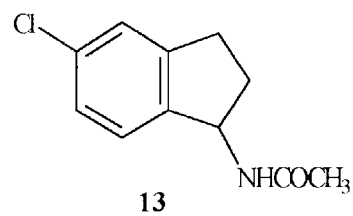

The present invention discloses a pharmaceutical composition which comprises a therapeutically effective amount of a compound having the structure:

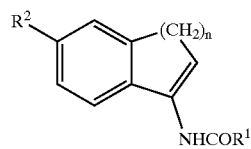

1 wherein n is 1 or 2, $R^1$ is hydrogen, a linear or branched chain $C_1$–$C_8$ alkyl or a linear or branched chain $C_1$–$C_8$ alkoxy and $R^2$ is hydrogen or a halogen and a pharmaceutically acceptable carrier.

In a specific embodiment of this invention, the therapeutically effective amount is 12.5 to 150 mg/kg.

In a specific embodiment of this invention, wherein the carrier is selected for a particular route of administration, the administration selected from the group consisting of oral, intravenous, intraperitoneal, intramuscular, subcutaneous, intra-articular, intra-nasal, intra-thecal, intra-dermal, trans-dermal and by inhalation.

In a specific embodiment, the halogen is chlorine.

In a specific embodiment of this invention, the compound is selected from the group consisting of: N-acetyl-3-amino-1H-indene; N-acetyl-4-amino-1,2-dihydronaphthalene; N-formyl-3-amino-1H-indene; N-acetyl-3-amino-6-chloro-1H-indene; N-formyl-6-chloro-3-amino-1H-indene; and N-methoxycarbonyl-3-amino-1H-indene.

In one embodiment of this invention, the compound has the structure:

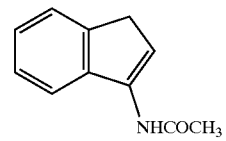

3

In another embodiment of this invention, the compound has the structure:

4

In another embodiment of this invention, the compound has the structure:

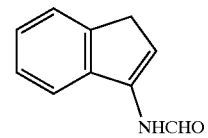

5

In another embodiment of this invention, the compound has the structure:

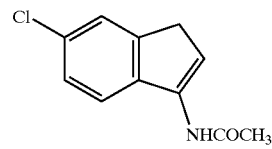

6

In another embodiment of this invention, the compound has the structure:

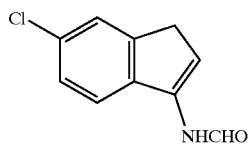

In still another embodiment of this invention, the compound has the structure:

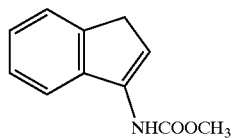

The present invention discloses compounds having the structure:

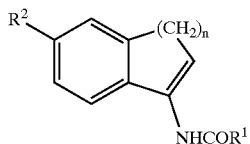

wherein n is 1 or 2, $R^1$ is hydrogen, a linear or branched chain $C_1$–$C_8$ alkyl or a linear or branched chain $C_1$–$C_8$ alkoxy and $R^2$ is hydrogen or a halogen; provided that where n is 1 and $R^1$ is isobutyl, $R^2$ cannot be H; that where n is 2, $R^1$ and $R^2$ both cannot be hydrogen; and that where $R^1$ is a methyl group, $R^2$ cannot be hydrogen.

The present invention discloses the method of treating a subject suffering from a disorder selected from the group consisting of Alzheimer's disease, head trauma, stroke, hypoxia, anoxia, epilepsy, convulsions, or seizures which comprises administering to the subject an amount of the compound having the structure:

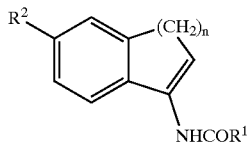

wherein n is 1 or 2, $R^1$ is hydrogen, branched or unbranched chain $C_1$–$C_8$ alkyl or a linear or branched chain $C_1$–$C_8$ alkoxy and $R^2$ is hydrogen or a halogen and a pharmaceutically acceptable carrier, effective to treat the disorder in the subject.

In one embodiment of the method of treating a subject suffering from a disorder, the disorder is Alzheimer's disease.

In one embodiment of the method of treating a subject suffering from a disorder, the disorder is head trauma.

In one embodiment of the method of treating a subject suffering from a disorder, the disorder is stroke.

In one embodiment of the method of treating a subject suffering from a disorder, the disorder is hypoxia.

In one embodiment of the method of treating a subject suffering from a disorder, the disorder is anoxia.

In one embodiment of the method of treating a subject suffering from a disorder, the disorder is epilepsy.

In one embodiment of the method of treating a subject suffering from a disorder, the disorder is convulsions.

In one embodiment of the method of treating a subject suffering from a disorder, the disorder is seizures.

In a specific embodiment of this invention, the method of treating head trauma, stroke, hypoxia, anoxia, epilepsy, convulsions, seizures, or Alzheimer's disease in a subject comprises administering to the subject a therapeutically effective amount of one of the following compounds: N-acetyl-3-amino-1H-indene; N-acetyl-3-amino-6-chloro-1H-indene; N-formyl-3-amino-1H-indene; N-formyl-6-chloro-1H-indene; N-formyl-3-amino-1H-indene; N-formyl-6-chloro-3-amino-1H-indene; and N-methoxycarbonyl-3-amino-1H-indene; N-acetyl-4-amino-1,2-dihydronaphthalene.

In an embodiment of the present invention, the administration of the method of treating head trauma, stroke, hypoxia, anoxia, epilepsy, convulsions, seizures, or Alzheimer's disease in a subject comprises oral, parenteral, topical, transdermal, rectal, nasal, or buccal administration.

In a specific embodiment, the pharmaceutical compositions of the present invention may be prepared as medicaments to be administered orally, parenterally, rectally, topically, transdermally, buccally, or nasally. Suitable forms for oral administration include tablets, compressed or coated pills, dragees, sachets, hard or gelatin capsules, sub-lingual tablets, syrups and suspensions; for parenteral administration the invention provides ampoules or vials tshat include an aqueous or non-aqueous solution or emulsion; for rectal administration there are provided suppositories with hydrophilic or hydrophobic vehicles; and for topical application as ointments or aerosol formulations known in the art; for transdermal delivery, there are provided suitable delivery systems as known in the art; and for nasal delivery there are provided suitable aerosol delivery systems known in the art.

A further embodiment of this invention includes selected compounds wherein the molecule is of relatively planar conformation compared to N-acetyl-1-aminoindan (structure 2) or its enantiomer (structure 2a). Accordingly, compounds 3, 5, 6, 7, and 8 represent preferred embodiments of the present invention wherein the objective is to enhance neuroprotection, as in the case of treating Alzheimer's disease.

Another embodiment of this invention comprises compounds 3, 4, 5, and 6 wherein the objective is to treat epilepsy or convulsions.

A further embodiment of this invention comprises compound 6 wherein the objective is to both enhance neuroprotection and treat epilepsy and convulsions.

A further preferred embodiment of this invention comprises using one of compounds 3, 5, or 6 wherein the objective is to provide neuroprotection for an extended period against neural injury in cases of stroke or trauma.

The present invention discloses a process for preparing a compound having the structure:

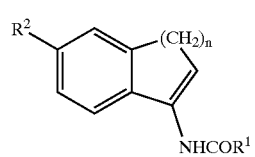

wherein n is 1 or 2, $R^1$ is hydrogen, branched or unbranched chain $C_1$–$C_8$ alkyl or a linear or branched chain $C_1$–$C_8$ alkoxy and $R^2$ is hydrogen or a halogen comprising steps A–D:

A. reacting an oxime or an aminoindan with a 5- or 6-membered heterocyclic amine to produce a residue;

B. admixing the residue of step (a) with sodium carbonate;

C. extracting the residue of step (b) with a suitable solvent such as an ether or an ester; and D. drying the residue of step (c) with a drying agent.

In one embodiment of the invention, the 5- or 6-membered heterocyclic amine is selected from a group consisting of pyridine, imidazole, and n-chlorosuccinimide.

In another embodiment of the invention, the oxime of step (a) reacts further with acetic anhydride.

In another embodiment of the invention, the oxime of step (a) reacts further with titanium triacetate.

In another embodiment of the invention, the suitable solvent of step (c) is an ether or an ester.

In further embodiment of the invention, the suitable solvent of step (c) is ethyl acetate.

In one embodiment of the invention, the drying agent of step (d) is magnesium sulfate.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example 1

N-Acetyl-3-amino-1H-indene (Structure 3)

1-Indanone oxime (2.33 g, 0.016 moles) and imidazole (78 mg) in acetonitrile (45 ml) cooled in ice, were treated with acetic anhydride (11 ml, 0.12 moles) and the mixture thus stirred for one hour. Titanium triacetate (17 g) was added, followed by more acetic anhydride (11 ml, 0.12 moles). The mixture was brought to reflux under nitrogen. After 2 hours the mixture was allowed to cool, poured into 1M sodium carbonate (250 ml) and stirred for 15 minutes. Three-fold extraction with ethyl acetate, drying ($MgSO_4$) and evaporation left a brown oil which was reevaporated with toluene. The brown residue was subjected to flash chromatography on silica gel with ethyl acetate/hexane 1:2 v/v. The major component was obtained as a white solid (1.7 g) from the appropriate fractions and was recrystallized from ethyl acetate/hexane to give the title compound, mp 137–138° C. (1.45 g, 52.9%).

Anal. required for $C_{11}H_{11}NO$: C, 76.27; H, 6.40; N, 8.09%. Found: C, 75.98; H, 6.48; N, 8.02%.

$^1$H NMR $\delta(CDCl_3)$: 7.5 (br s, 1H, NH) and 7.47 (d, J=7 Hz, 1H, C7-H), 7.2–7.26 (m, 3H, C4, 5, 6-H), 6.87 (t, J=2.5 Hz, 1H, C2-H), 3.42 (d, J=2.4 Hz, C1-$H_2$), 2.24 (s, 3H, Me).

MS (Cl/$NH_3$): 174 (MH$^+$, 100%)

IR: 3273, 3060, 2886, 1682, 1562, 1279, 782, 764, 727 cm$^{-1}$.

Example 2

N-Acetyl-3-amino-1H-indene (Structure 3)

1-Indanone oxime (7.02 g, 0.048 moles), pyridine (250 ml) and acetic anhydride (170 ml) were stirred and heated under nitrogen at reflux for 16.5 hours. The cooled mixture was evaporated in vacuo and the residue agitated thoroughly with 1N sodium carbonate solution and ether (250 ml each). The liquid was filtered through filter-aid and the black solid treated again with sodium carbonate/ether and filtered. The combined ether extracts and washes were dried ($MgSO_4$) and evaporated to a black-orange oil (8.6 g). This was applied to a column of basic alumina, allowed to stand for 2.5 hours and eluted with ethyl acetate/hexane 1:2 v/v. The appropriated fractions were evaporated to leave a crude solid (3 g). This was recrystallized from ethyl acetate/hexane to give the title product, mp. 139° C., (1.44 g, 17%) with the same IR spectrum as in Example 1.

Example 3

N-Acetyl-3-amino-6-chloro-1H-indene (Structure 6)

By the same procedure as in Example 1, 5-chloro-1-indanone oxime (2.27 g, 0.0125 moles) gave a solid residue which was recrystallized from toluene to give the title compound (1.58 g, 60.9%), mp 181–2° C.

Anal. $C_{11}H_{10}ClNO$ requires: C, 63.63; H, 4.85; Cl, 17.07; N, 6.75%. Found: C, 63.57; H, 4.29; Cl, 17.20; N, 6.52%.

1H NMR $\delta(CDCl_3)$: 7.45 (d, J=1Hz, 1H, C7-H), 7.30 (dd, J=1.8 and 8.1 Hz, 2H, C5-H and NH), 7.16 (d, J=8 Hz, 1H,C4-H), 6.86 (t, J=2 Hz, 1H, C2-H), 3.42 (d, J=2 Hz, 2H, C1-$H_2$), 2.24 (s, 3H, Me).

MS (Cl/$NH_3$): 210, 208, (30, 100%, MH$^+$)

IR: 3328, 1670, 1550, 1268, 824, 774, 690 cm$^{-1}$.

Example 4

N-Acetyl-4-amino-1,2-dihydronaphthalene (Structure 4)

By the same procedure as in Example 1, α-tetralone oxime (2.24 g, 0.014 moles) gave an oily residue which was applied to a column of basic alumina (387 g) prepared in ethyl acetate/hexane 1:1 v/v. After two hours, elution with this solvent gave a small fast fraction and then the major product (1.0 g after evaporation of the fractions). It was recrystallized from toluene (8 ml) to give the title compound, mp 137–8° C., (0.86 g, 33%).

Anal. $C_{12}H_{13}NO$ requires C, 76.98; H, 6.97; N, 7.48%. Found: C, 76.81; H, 7.08; N, 7.43%.

$^1$H NMR $\delta(CDCl_3)$ (assignments to the E- and Z-rotamers are marked E and Z respectively): 7.05–7.28 (m, 4H, C5, 6, 7, 8-$H_4$), 6.82 (br s, 0.7H, ZNH): 6.67 (br s, 0.3H, ENH), 6.44 (t, J=4.5 Hz, 0.7H, ZC3-H), 5.97 (br t, J=5 Hz, 0.2H, EC3-H), 2.83 (br t, J=8 Hz, EC2-H) and 2.77 (t, J=8 Hz, ZC2-H) (total, 3H), 2.25–2.50 (m, 2H, C1-$H_2$) 2.16 (s, 2.1H,Z-$CH_3$), 1.95 (s, 0.8H, E-$CH_3$).

MS (Cl\$NH_3$): 188 (100%, MH$^+$)

IR: 3250, 3025, 2931, 1657 (vs) 1635, 1569, 1523, 1285, 817, 771, 733 cm$^{-1}$.

Example 5

N-Formyl-3-amino-1H-indene (Structure 5)

1-Indanone oxime (2.25 g, 0.015 moles) and imidazole (40 mg) in acetonitrile (60 ml) cooled in ice, were treated with formic-acetic anhydride (11 ml) and the mixture thus stirred for one hour. Titanium triacetate (18 g) was added, followed by more formic acetic anhydride (11 ml, 0.12 moles). The same work-up as in Example 1 left a brown oil which was titrated with hexane to form a brown solid (2.24 g).

Such material (2.69 g) was subjected to flash chromatography on silica gel (elution with ethyl acetate/hexane 1:3 v/v) and the solid obtained was recrystallized from toluene/hexane to give the title compound, mp 87.5–88.5° C., (1.58 g, adjusted yield: 54%).

Anal. $C_{10}H_9NO$ requires C, 75.45; H, 5.70; N, 8.80%. Found: C, 75.63, H, 5.77; N, 9.11%.

1H NMR δ($CDCl_3$) (assignments to the E- and Z-rotamers are marked E and Z respectively): 8.78 (d, J=11.4 Hz, ECHO), 8.53 (d, J=1.2 Hz, ZCHO), 8 (v br d, J=11, ENH), 7.55 (br, ZNH), 7.49 (d, J=7.5 Hz C4-H), 7.2–7.4 (m, C5,6,7-$H_3$), 6.92 (t, J=2.4 Hz, ZC2-H, 6.11 (t, J=2.2 Hz, EC2-H), 3.46 (d, J=2.4 Hz, ZC1-$H_2$), 3.43 (d, J=2.1 Hz, EC1-$H_2$). The areas of Z:E signal were in all the ratio 1.45:1.

MS (Cl/$NH_3$): 160 (100%, $MH^+$).

IR: 3261, 3218, 3066, 2870, 1710, 1683, 1587, 1560, 1406, 1390, 756, 711 $cm^{-1}$.

Example 6

N-formyl-6-chloro-3-amino-1H-indene (Structure 7)

By the same procedure as in Example 5, 5-chloro-1-indanone oxime (2.23 g, 0.012 moles) gave a brown solid (2.1 g). Such material (3.86 g) was subjected to flash chromatography on silica gel (520 g) with ethyl acetate/petrol ether 2:3 v/v and the solid obtained, after treatment with active charcoal in ethyl acetate, was recrystallized from toluene/hexane to give the title compound, mp. 155° C., (2.08 g, 44.9% adjusted yield).

Anal. $C_{10}H_8ClNO$ requires C, 62.03; H, 4.16; Cl, 18.31; N, 7.23%. Found: C, 61.81; H, 4.19; Cl, 17.91; N, 6.98%.

1H NMR δ(DMSO-$d_6$), (assignments to the E- and Z-rotamers are marked E and Z respectively): 10.36 (br s, ZNH); 10.22 (br d, J=11 Hz, ENH); 8.79 (d, J=11 Hz, ECHO); 8.4 (d, J=1.8 Hz, ZCHO); 7.66 (d, J=8 Hz, ZC4-H); 7.64 (d, J=8 Hz, EC4-H); 7.56 (d, J=1.5 Hz, ZC7-H);7.54 (sh. EC7-H); 7.42 (dd, J=8, 1.8 Hz, ZC5-H); 7.38 (d, J=2 Hz, half of dd, EC5-H); 6.8(t, J=2.5 Hz, ZC2-H); 6.24 (t, J=2.5 Hz, EC-2H); 3.44 (d, J=2.4 Hz, ZC1-H); 3.42 (d, J=2.4 Hz, EC1-H); The areas of Z:E signals were in the ratio 6:1.

MS(Cl/$CH_4$): 196, 194 (35, 100%, $MH^+$)

IR: 3262, 1701, 1666, 1605, 1577, 1558, 1394, 856, 803, 772 $cm^{-1}$.

Example 7

N-Methoxycarbonyl-3-amino-1H-indene (Structure 8)

N-Chlorosuccinimide (7.32 g, 0.055 moles) was added in portions to a stirred solution of 1-aminoindan (6.64 g, 0.05 moles) in dichloromethane (190 ml). After 1.25 hours the clear solution was washed thrice with water and the organic phase dried ($MgSO_4$).

Methanol (50 ml) was added before concentration down to ca 20 ml, the bath temperature being restricted to 35° C. The residual methanolic solution was added to a solution of sodium (1.5 g, 0.07 g atoms) in methanol (60 ml). This mixture was refluxed for 12 minutes, toluene (30 ml) was added and the methanol evaporated in vacuo (bath at 40° C.) to a small volume. This was treated with a solution of dimethyl pyrocarbonate (8.9 ml, 0.08 moles) in toluene (60 ml). The mixture was stirred at rt for ca 0.75 hrs, diluted with ethyl acetate (100 ml) and extracted twice with water. The dried organic layer left a dark brown oil. Flash chromatography on silica gel (595 g) with ethyl acetate/petrol ether 1:5 v/v gave a brown solid. The material was recrystallized from refluxing cyclohexane (25 ml) and hexane (10 ml) to give the title compound, mp. 88° C. (4.34 g, 45.9%).

Anal. $C_{11}H_{11}NO_2$ requires: C, 69.82; H, 5.86; N, 7.42%. Found: C, 69.58; H, 5.71; N, 7.50%.

1H NMR δ(DMSO-$d_6$): 9.60 (br s, 1H, NH); 7.79 (d, J=7 Hz, 1H, C4-H); 7.45(d, J=7 Hz 1H,C7-H); 7.28 (t, J=7 Hz) and 7.21 (t,J=7 Hz) (together 2H, C6-H and C5-H); 6.46 (br s, 1H, C2-H); 3.71) (s, 3H, OMe); 3.36(d, J=2.4 Hz, C1-$H_2$).

MS (Cl/$NH_3$): 190 (100%, $MH^+$)

IR: 3331, 2949, 1731, 1708, 1579, 1548, 1238, 1036, 759, 716, 649 $cm^{-1}$.

The following EXAMPLES and their accompanying Tables and FIGS. relate to the Biological Experiments carried out in accordance with this invention.

Example 8

Protection Against Hypobaric Hypoxia in Mice

Experimental Protocol

The apparatus used consisted of two chambers A and B connected by a three-way valve. Chamber A had a volume of 12 L and was connected to a vacuum pump. Chamber B had a volume of 2.5 L. Initially, four mice were placed in chamber B which contained room air at normal atmospheric pressure. The air in chamber A was evacuated to a pressure of 100 mm Hg. The three way valve was turned to disconnect chamber B from room air and to connect it to chamber A. At this point, the pressure in B fell to 200 mm Hg. Survival of residing mice was determined up to a maximum exposure of 15 minutes, and is defined as the time between onset of hypoxia to cessation of respiration.

Results

The survival time as percent of vehicle-treated controls ±SD is given in Table 1 for representative members of the N-acyl-3-amino-1H-indene series, some corresponding members of the N-acyl-1-aminoindan series, and two reference drugs, nembutal and diazepam:

TABLE 1

Increase in survival time, as percent of vehicle control, by test drugs in the hypobaric hypoxia test

| Drug | mg/kg, ip | n | survival ± SD | p< |
|---|---|---|---|---|
| Saline/vehicle | | 8 | 100 | |
| 2a | 100 | 8 | 375 ± 72 | 0.001 |
| | 50 | 4 | 299 ± 69 | 0.05 |
| | 36 | 8 | 110 ± 57 | N.S. |
| | 25 | 8 | 142 ± 94 | N.S. |
| 2 | 100 | 8 | 200 | N.S. |
| 3 | 100 | 8 | 703 ± 242 | 0.001 |
| | 50 | 8 | 879 ± 237 | 0.001 |
| | 25 | 8 | 735 ± 238 | 0.001 |
| | 12.5 | 8 | 637 ± 341 | 0.001 |
| 5 | 100 | 8 | 489 ± 286 | 0.001 |
| | 50 | 8 | 331 ± 272 | 0.05 |
| | 25 | 8 | 586 ± 253 | 0.001 |
| | 12.5 | 12 | 248 ± 154 | 0.05 |
| 6 | 100 | 8 | 294 ± 267 | 0.05 |
| | 50 | 8 | 234 ± 120 | 0.05 |
| | 25 | 8 | 393 ± 110 | 0.0001 |
| 4 | 25 | 8 | 156 ± 24 | N.S. |
| 7 | 50 | 8 | 893 ± 433 | 0.0005 |
| | 25 | 8 | 467 ± 239 | 0.001 |
| | 12.5 | 16 | 357 ± 299 | 0.005 |
| 8 | 50 | 8 | 547 ± 327 | 0.05 |
| | 25 | 12 | 402 ± 348 | 0.05 |
| | 12.5 | 8 | 195 ± 90 | 0.05 |

TABLE 1-continued

Increase in survival time, as percent of vehicle control, by test drugs in the hypobaric hypoxia test

| Drug | mg/kg, ip | n | survival ± SD | p< |
|---|---|---|---|---|
| 13 | 100 | 4 | 267 ± 151 | 0.05 |
|  | 50 | 4 | 148 ± 77 | 0.05 |
| Nembutal | 40 | 8 | 253 ± 200 | 0.005 |
| Diazepam | 10 | 8 | 316 ± 78 | 0.003 | n = number of animals; SD = standard deviation; p = statistical significance

The hypobaric hypoxia test clearly shows that members of the N-acyl-1-amino-1-indene series are potent neuroprotective agents. In particular, 3 is far more potent than either of its corresponding members in the N-acylaminoindan series, N-acetyl-1-(R)-aminoindan (2a) and N-acetyl-1-(S)-aminoindan (2), indicating that a particular molecular shape and conformation, especially planarity, are essential for optimal neuroprotective activity. This property is shared by 5 which is the N-formyl analog of 3, and by 6 which is the chloro derivative of 3, confirming the dependence of activity on molecular planarity.

Example 9

Protection Against Electroshock-induced Seizure in Mice

Experimental Protocol

Male ICR mice were used. The rodent shocker apparatus consisted of a shock stimulator Type 221 (Hugo Sachs Elektronik, Germany) with a current setting for mice. Thirty minutes after medication with a given agent, given intraperitoneally as a fine slurry in methyl cellulose 0.5% in distilled water, each mouse received an electroshock of 50 mA for 0.2 seconds, applied to the eye, at a maximum of 250 V/300 mA. The ratio of mice protected against seizure in a group of four per dose was determined and used as an indicator of neuroprotective activity.

Results

Table 2 shows the potencies of various 3-amino-1H-indenes in comparison to a reference standard, sodium valproate.

TABLE 2

Potency of N-acyl-3-amino-1H-indenes in protecting mice against maximal electroshock

| Compound | mg/kg | protected/ total | $ED_{50}$ (95% confidence limits) |
|---|---|---|---|
| Vehicle control | 0.5 mL | 0/4 |  |
| 2a | 25 | 0/4 | 42 (29.9–59.1) |
|  | 50 | 3/4 |  |
|  | 100 | 4/4 |  |
| 3 | 100 | 1/4 | 116.1 (96.1–140.3) |
|  | 125 | 2/4 |  |
|  | 150 | 4/4 |  |
| 6 | 50 | 2/4 | 50.0 (33.8–74.0) |
|  | 100 | 4/4 |  |
| 5 | 50 | 0/4 | 79.4 (65.1–96.9) |
|  | 75 | 1/4 |  |
|  | 100 | 4/4 |  |
| 4 | 75 | 0/4 | 92.3 (80.2–106.3) |
|  | 100 | 3/4 |  |

TABLE 2-continued

Potency of N-acyl-3-amino-1H-indenes in protecting mice against maximal electroshock

| Compound | mg/kg | protected/ total | $ED_{50}$ (95% confidence limits) |
|---|---|---|---|
| Sodium valproate | 280 | 1/8 | 350 |
|  | 310 | 2/8 |  |
|  | 340 | 4/8 |  |
|  | 400 | 6/8 |  |
|  | 600 | 8/8 |  |

$ED_{50}$ = median effective dose

The MES test shows that most test compounds are of comparable potency to sodium valproate, a known and potent anti-epileptic agent. It is noteworthy that the potency of compound 6 is within the same range as that of compound 2a, but is far more potent in the hypobaric hypoxia test at low doses. This indicates that compound 6 is a superior neuroprotectant than compound 2a.

Example 10

Decrease of Response to Electric Stimulation in the Guinea-pig Ileal Preparation Experimental Protocol A 2 cm-long section of the distal ileum freshly dissected from a $CO_2$-asphyxiated guinea pig is cleaned from adhering tissue and mounted in an organ bath (5 mL) containing Krebs solution constantly aerated with oxygen containing 5% $CO_2$. The initial tension is adjusted at 5 g per strip. Tension is monitored isometrically with a Grass FTC3 force transducer. Intramural electric stimulation is delivered through a platinum electrode from a Grass stimulator model s88, s44 at supramaximal voltage (V) and a frequency of 0.1/s. The preparation develops a rhythmic contractile response at maximal amplitude which is stable over time. Addition of test drugs to the organ bath causes a dose-dependent decrease in contraction amplitude which is stable over 5–8 minutes. The relative decrease in contractile response indicates the relative potency of a given agent in a series.

Results

Figure 2:
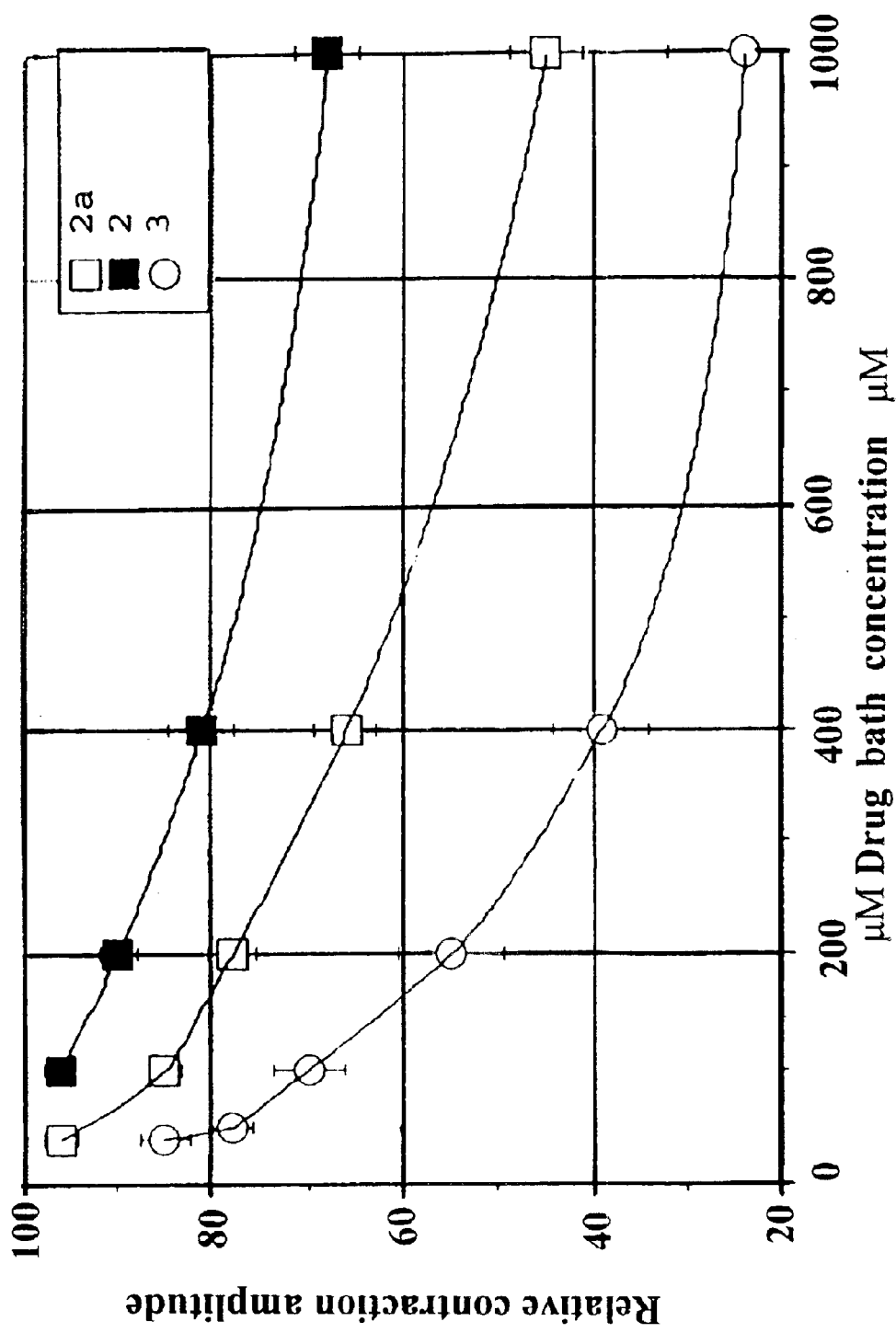
FIG. 2: Contractile response to intramural electric stimulation of the guinea pig ileal preparation in the presence of (R)-N-acetyl-1-aminoindan (2a), N-acetyl-1-aminoindan (2), N-acetyl-3-amino-1H-indene (3).
Figure 3:
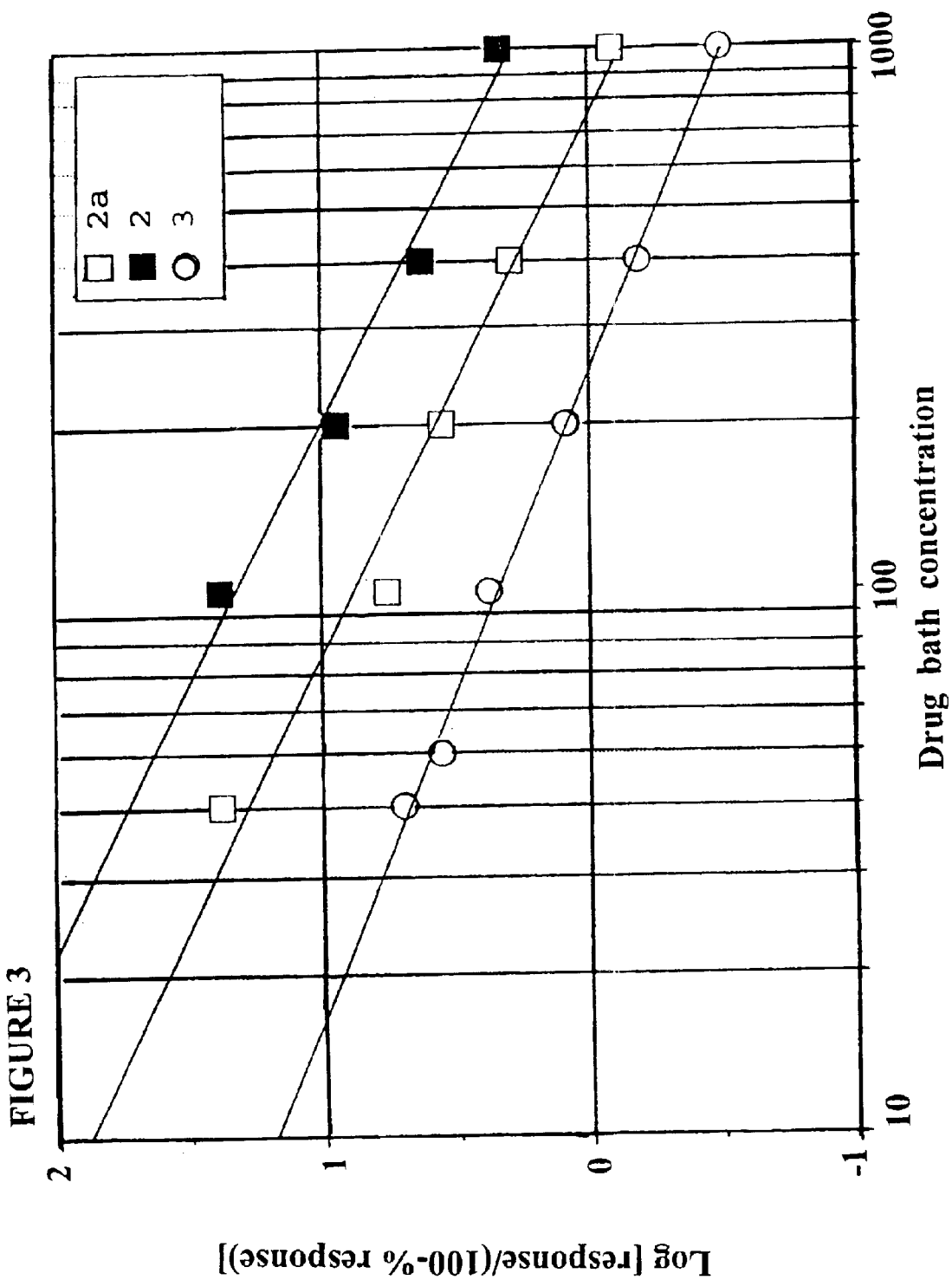
FIG. 3: Logit plot of the effect of (R)-N-acetyl-1-aminoindan (2a), N-acetyl-1-aminoindan (2), and N-acetyl-3-amino-1H-indene (3) on the contractile response to intramural electric stimulation of the guinea-pig ileal preparation, corresponding to FIG. 2.

FIG. 2 shows the effect of compound 3 in relation to that of either compounds 2a and 2 which are its analogues in the aminoindan series. Logit plots (as described by R. B. Barlow, Quantitative Aspects of Chemical Pharmacology, Croom Helm, London 1980, pp 120–121) of the same data are shows in FIG. 3 and allow one to calculate the corresponding EC50's values which are given in Table 3.

Figure 4:
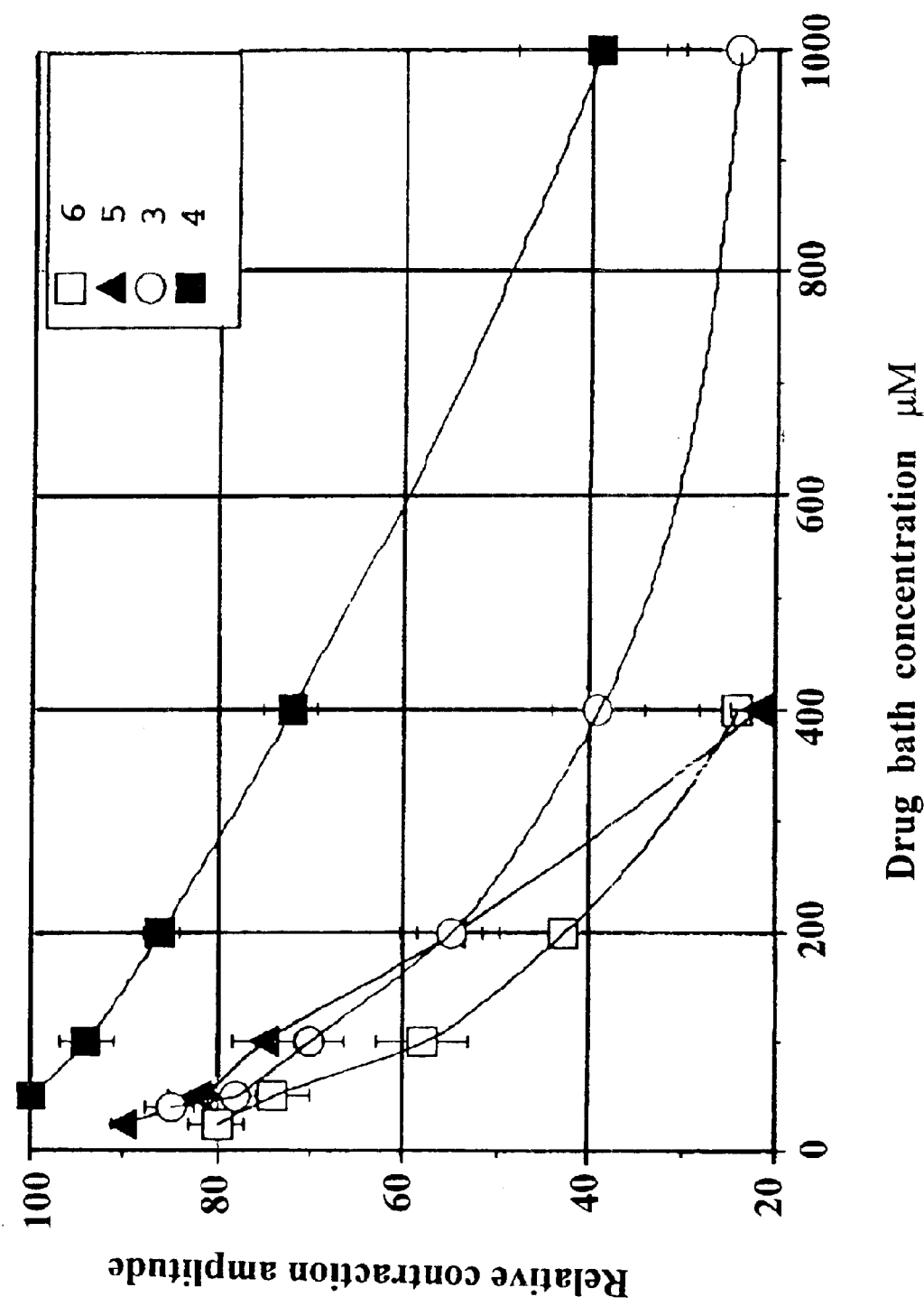
FIG. 4: Contractile response to intramural electric stimulation of the guinea-pig ileal preparation in the presence of N-acetyl-3-amino-6-chloro-1H-indene (6), N-formyl-3-amino-1H-indene (5), N-acetyl-3-amino-1H-indene (3), N-acetyl-4-amino-1,2-dihydronaphthalene (4).
Figure 5:
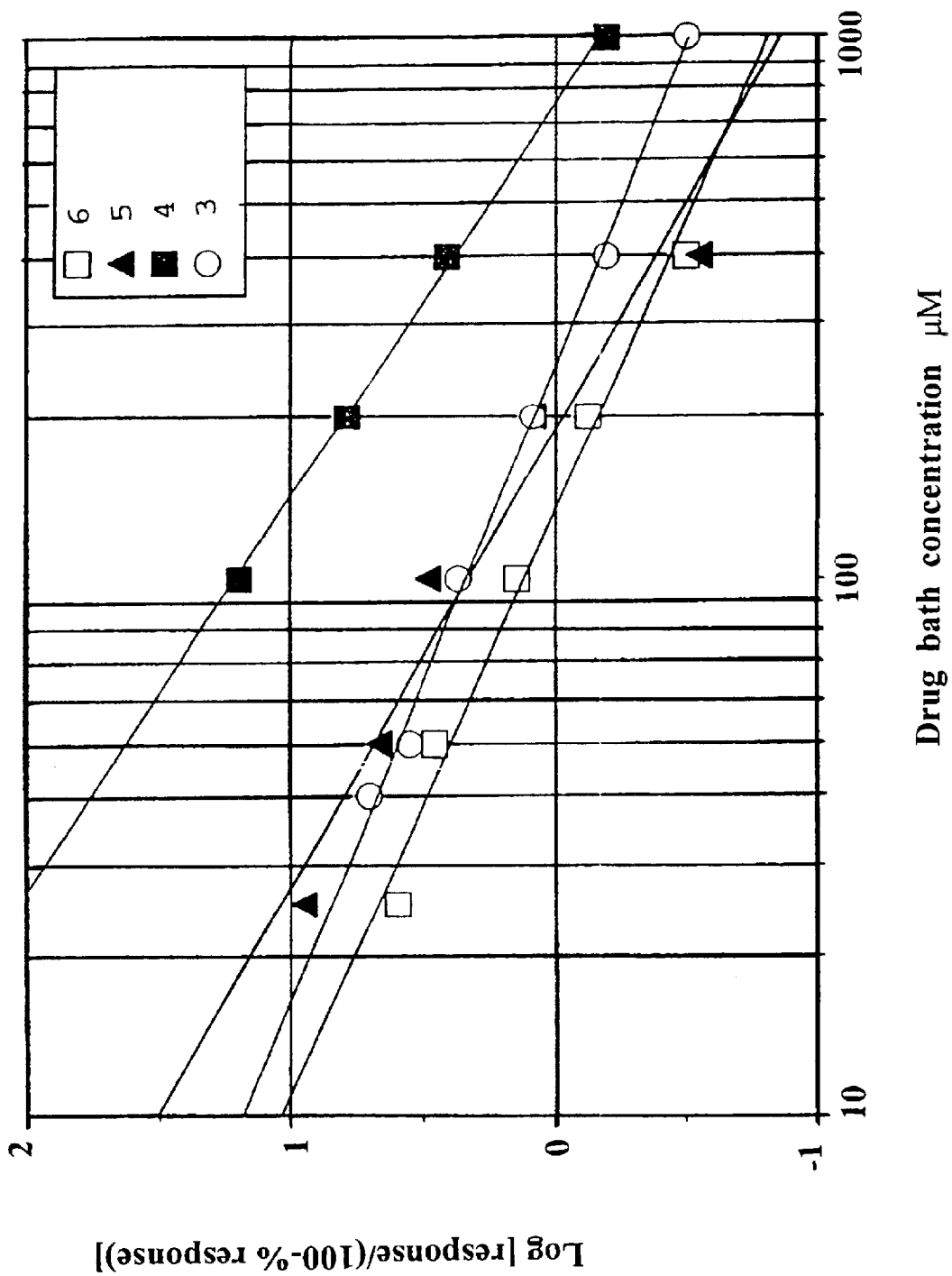
FIG. 5: Logit plot of the effect of N-acetyl-3-amino-6-chloro-1H-indene (6), N-formyl-3-amino-1H-indene (5), N-acetyl-4-amino-1,2-dihydronaphthalene (4) and N-acetyl-3-amino-1H-indene (3) on the contractile response to intramural electric stimulation of the guinea-pig ileal preparation, corresponding to FIG. 4. X-axis: drug bath concentration expressed as micromoles per liter; Y-axis: log % response/(100-% response).

FIG. 4 shows the effect of other N-acyl-3-amino-1H-indenes 6 and 5 and also that of the analogous tetralene analog 4 in this test. The corresponding logit plots are shown in FIG. 5 and the relevant parameters are shown in Table 3.

TABLE 3

Logit plot parameters of the dose-effect relationship of test compounds on the contractile response of the guinea-pig ileal preparation to intramural electric stimulation

| Drug | linear regression fit | $EC_{50}$ |
|---|---|---|
| 2a | y = 2.8863–1.0042 log uM ($R^2$ = 0.981) | 748 uM |
| 2 | y = 3.3981–1.0406 log uM ($R^2$ = 0.977) | 1842 uM |
| 3 | y = 2.0324–0.8467 log uM ($R^2$ = 0.996) | 251 uM |

TABLE 3-continued

Logit plot parameters of the dose-effect relationship of test compounds on the contractile response of the guinea-pig ileal preparation to intramural electric stimulation

| Drug | linear regression fit | $EC_{50}$ |
|---|---|---|
| 6 | y = 1.9587–0.9222 log uM ($R^2$ = 0.981) | 133 uM |
| 5 | y = 2.6992–1.1869 log uM ($R^2$ = 0.946) | 188 uM |
| 4 | y = 3.9497–1.3732 log uM ($R^2$ = 0.998) | 752 uM |

The electrostimulation data of Table 3 show that compound 3 is more potent than either of its corresponding analogs in the aminoindan series. This result is consistent with the results from the hypobaric hypoxia test and the maximal electroshock-induced seizure test described above.

Further, compounds 6, 5, and 3 are more potent than 2a which is more potent than compounds 2 and 4. Of the three compounds, 6, 5, and 3, compounds 6 and 5 appear to be closer in activity than either of them to compound 3.

Example 11

Decrease in Response of Nerve Stimulation Evoked by a Nicotinic Agonist

Experimental Protocol

A strip of guinea-pig ileum is mounted in an organ bath, as described in EXAMPLE 10. 1-N,N-dimethyl-4-N-phenylpiperazinium chloride (DMPP) is added at intervals of about 15 minutes in order of increasing dose, to cause bath concentrations in the range of 0.1–10 uM. A brief contraction follows each addition. The amplitude of the contractile response is used to derive a dose-response relationship for DMPP. Usually, a bath concentration of 1 uM DMPP will give 90–100% of the maximal response obtainable in the given preparation. One of two procedures follows this: A dose-response of a test compound is determined in the presence of a fixed concentration of DMPP. This is done by incubating the preparation with a given concentration of the test compound, then challenging it with DMPP at a dose to give 1 uM bath concentration. The procedure is repeated with the next higher concentration of the test compound. In the other procedure, the dose-response of DMPP is determined in the presence of a fixed bath concentration of the test compound, usually 200 uM.

Results

Figure 6:
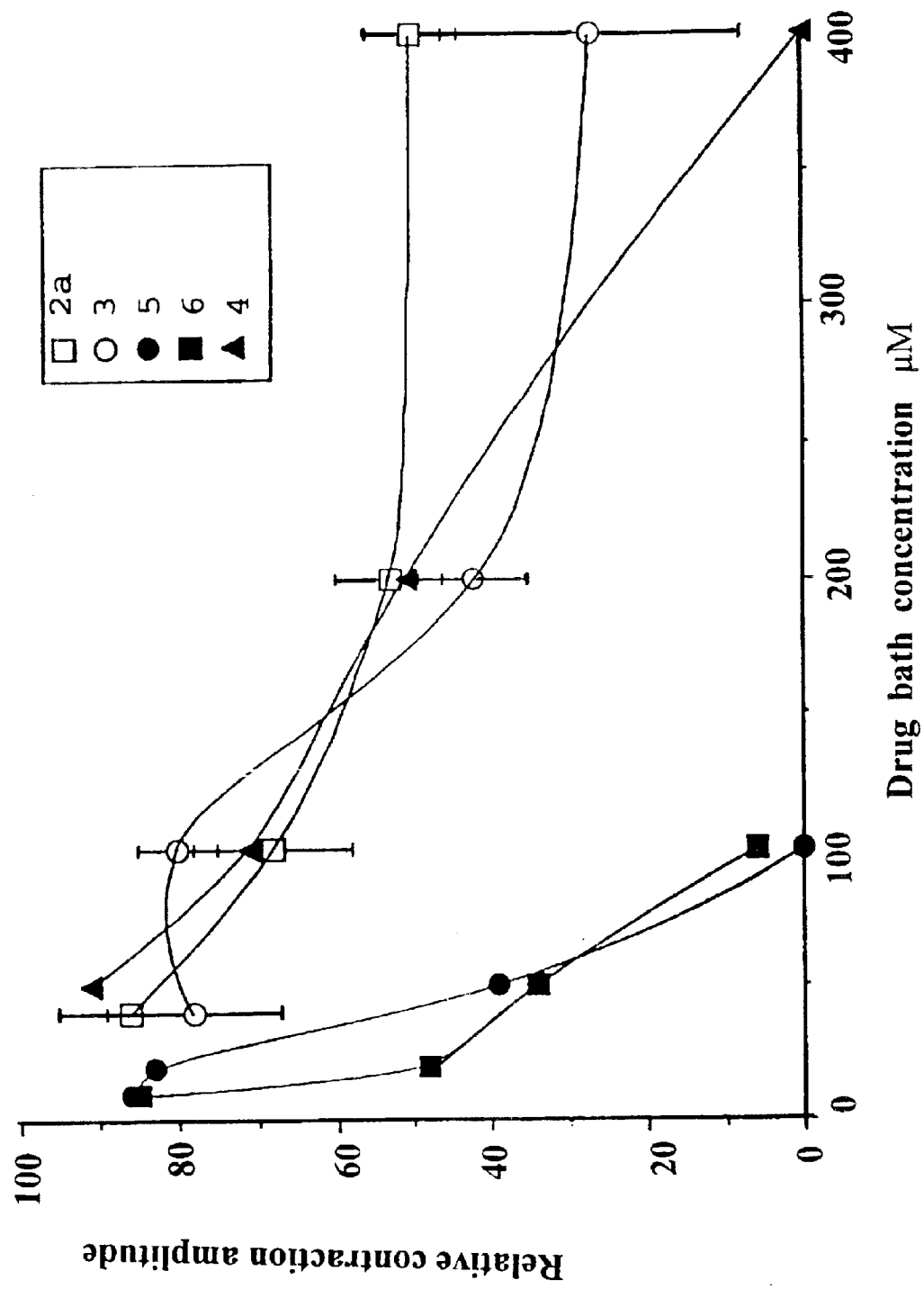
FIG. 6: Contractile response to dimethylphenylpiperazinium chloride (DMPP), 1 µM, in the presence of rising concentrations of (R)-N-acetyl-1-aminoindan (2a), N-acetyl-3-amino-1H-indene (3), N-acetyl-3-amino-6- chloro-1H-indene (6), N-formyl-3-amino-1H-indene (5) N-acetyl-4-amino-1,2-dihydronaphtahalene (4).
Figure 7A:
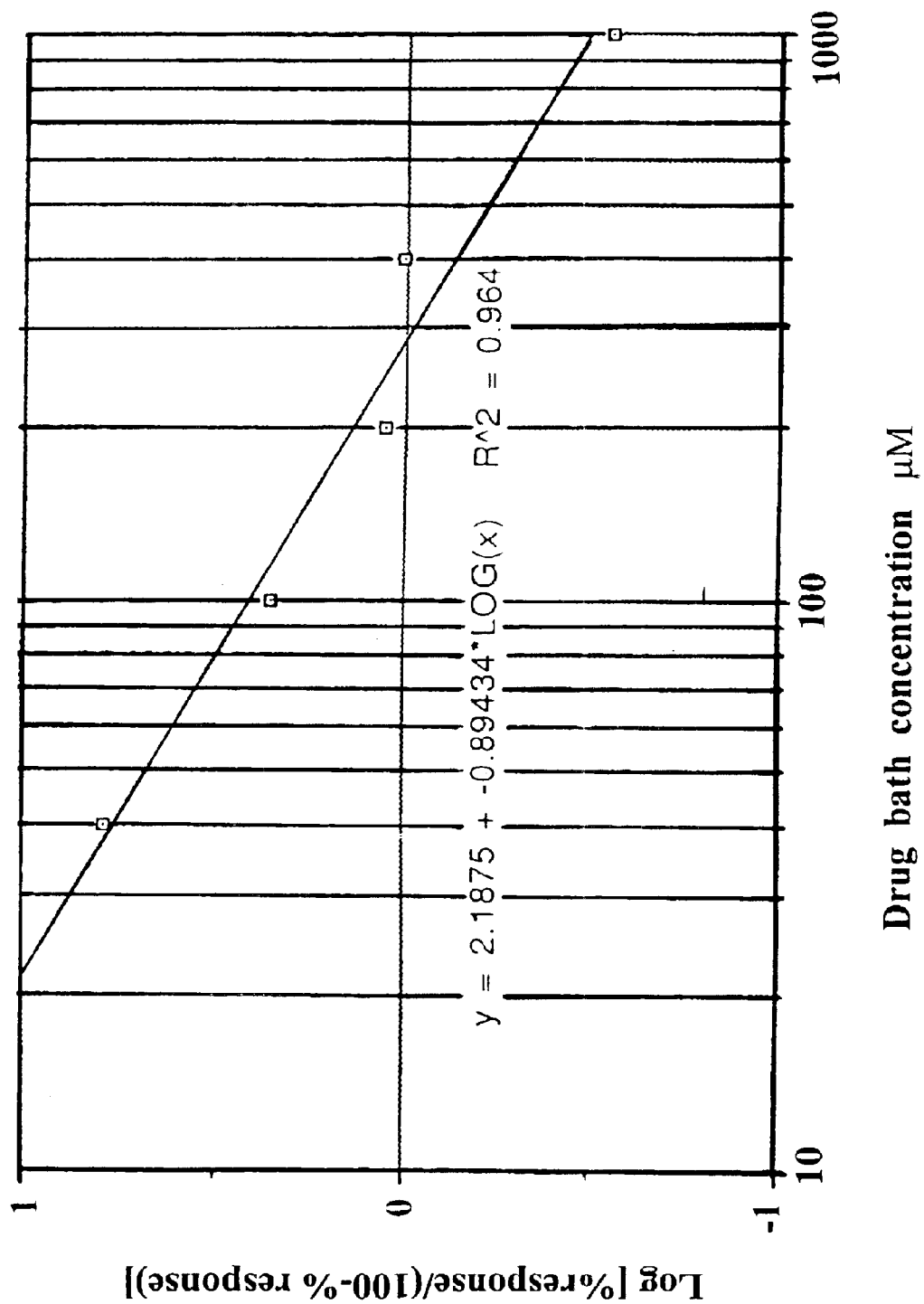
FIG. 7a: Logit plot of (R)-N-acetyl-1-aminoindan (2a) on the contractile response of the guinea-pig ileum to DMPP 1 μM, corresponding to FIG. 6. X-axis: drug bath concentration expressed as micromoles per liter; Y-axis: log % response/(100-% response).
Figure 7B:
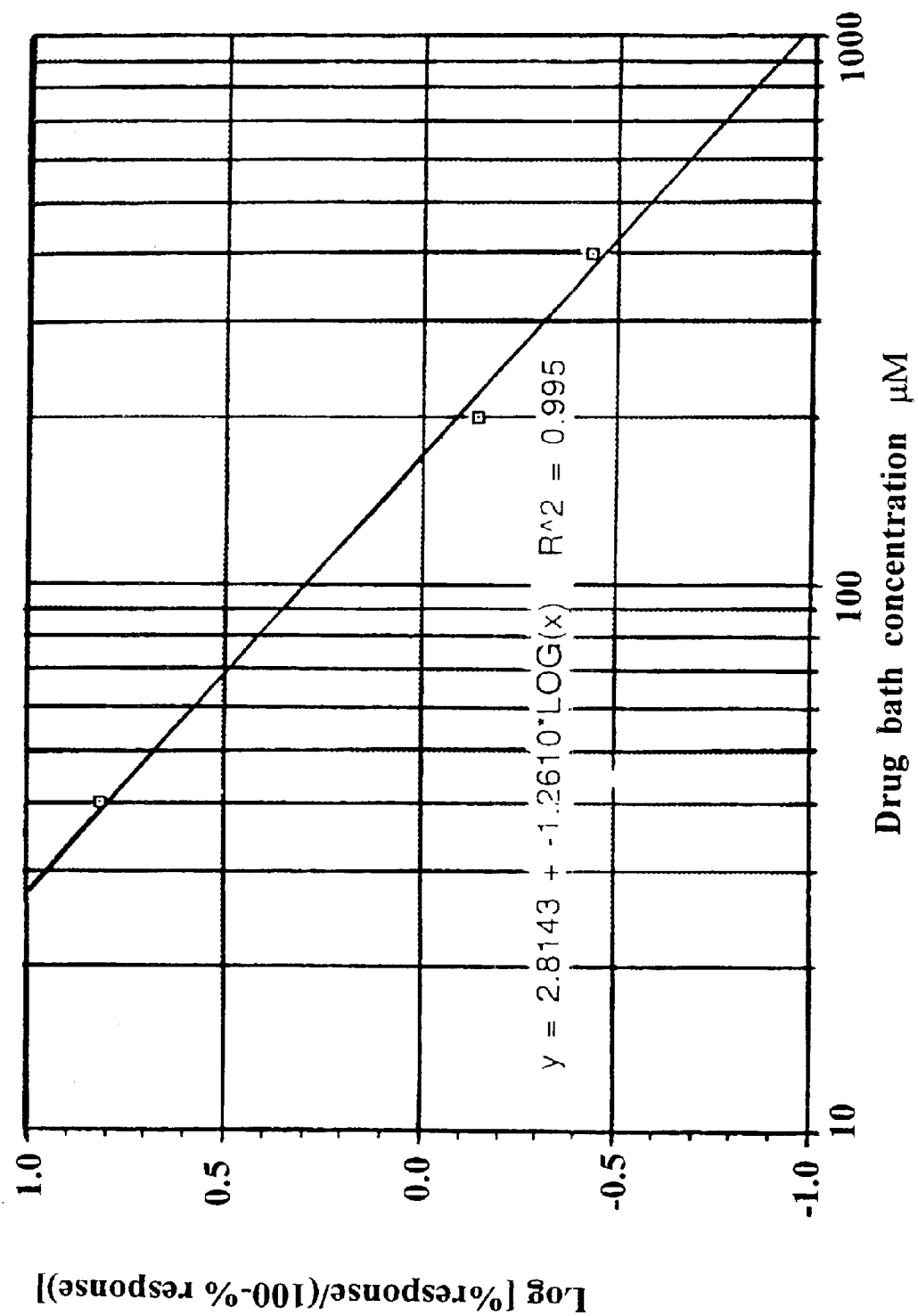
FIG. 7b: Logit plot of N-acetyl-3-amino-1H-indene (3) on the contractile response of the guinea-pig ileum to DMPP 1 μM, corresponding to FIG. 6 (with omission of data of 100 μM). X-axis: drug bath concentration expressed as micromoles per liter; Y-axis: log % response/(100-% response).
Figure 7C:
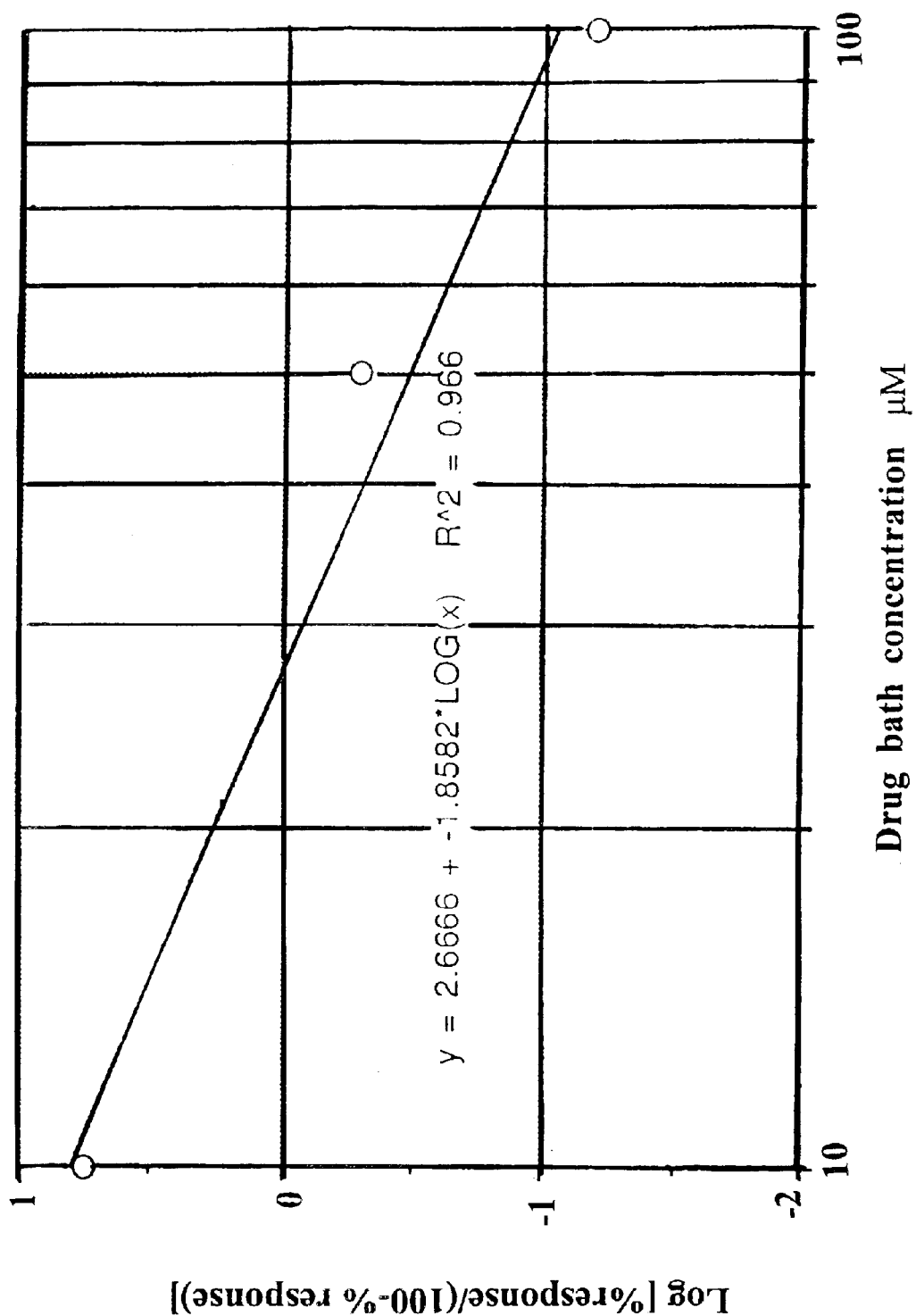
FIG. 7c: Logit plot of N-acetyl-3-amino-6-chloro-1H-indene (6) on the contractile response of the guinea-pig ileum to DMPP 1 μM, corresponding to FIG. 6 (with omission of data of 20 μM). X-axis: drug bath concentration expressed as micromoles per liter; Y-axis: log % response/ (100-% response).
Figure 7D:
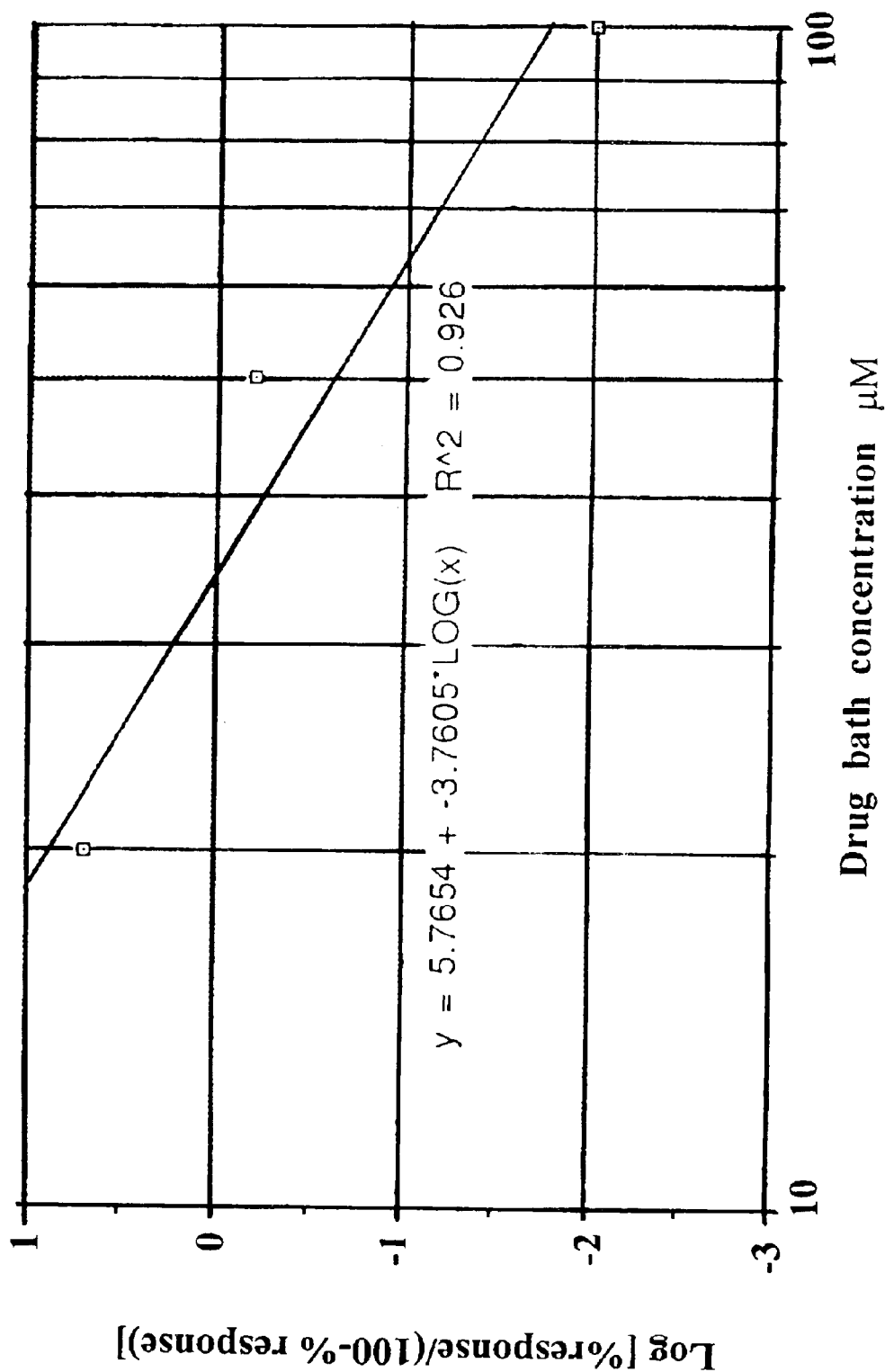
FIG. 7d: Logit plot of N-formyl-3-amino-1H-indene (5) on the contractile response of the guinea-pig ileum to DMPP 1 μM, corresponding to FIG. 6 (with omission of data of 10 μM). X-axis: drug bath concentration expressed as micromoles per liter; Y-axis: log % response/(100-% response).
Figure 7E:
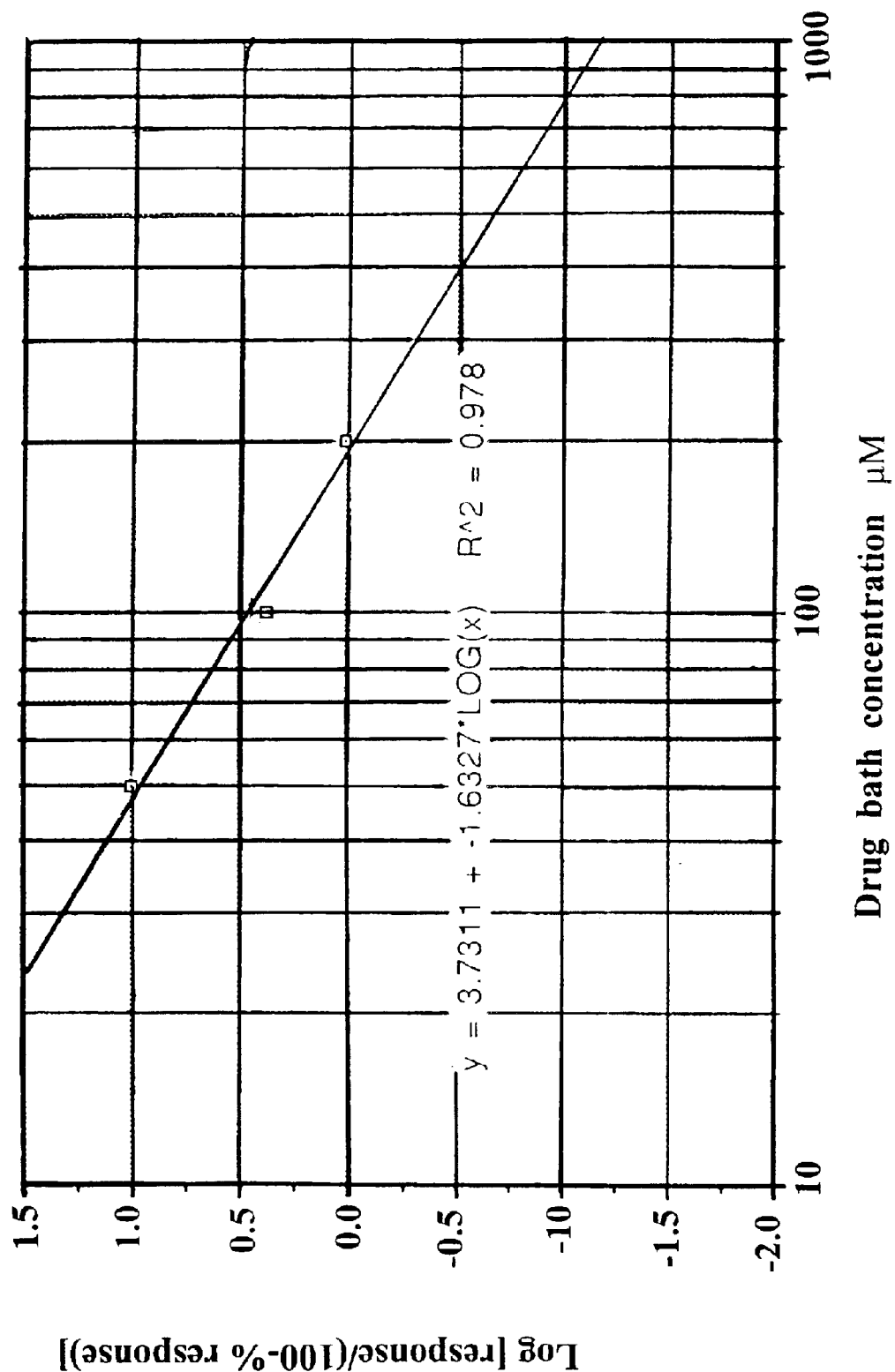
FIG. 7e: Logit plot of N-acetyl-4-amino-1,2-dihydronaphthalene (4) on the contractile response of the guinea-pig ileum to DMPP 1 μM, corresponding to FIG. 6 (with omission of data of 400 μM). X-axis: drug bath concentration expressed as micromoles per liter; Y-axis: log % response/(100-% response).

For the first procedure, FIG. 6 gives the effect of rising concentrations of either compounds 2a and 3 on the contractile response elicited by 1 uM DMPP. One sees a depression of the effect of DMPP in both cases, but the depression due to compound 3 is more profound that due to compound 2a. Compounds 6 and 5 are even more potent in this respect than compound 3; but compound 4 is less potent. FIGS. 7a–7e give the corresponding logit plots. The calculated EC50's values are given in Table 4:

TABLE 4

Parameters of the logit plot pertaining to the dose response relationship of test compounds in inhibiting the contractile response of the guinea-pig ileal preparation to 1 uM DMPP

| Test cmpd | linear regression fit | $EC_{50}$ |
|---|---|---|
| 2a | y = 2.1875–0.8943 log x, $R^2$ = 0.964 | 279 uM |
| 3 | y = 2.8143–1.2610 log x, $R^2$ = 0.995 | 170 uM |
| 6 | y = 2.6666–1.8582 log x, $R^2$ = 0.996 | 27 uM |

TABLE 4-continued

Parameters of the logit plot pertaining to the dose response relationship of test compounds in inhibiting the contractile response of the guinea-pig ileal preparation to 1 uM DMPP

| Test cmpd | linear regression fit | $EC_{50}$ |
|---|---|---|
| 5 | y = 5.7654–3.7605 log x, $R^2$ = 0.926 | 34 uM |
| 4 | y = 3.7311–1.6327 log x, $R^2$ = 0.978 | 193 uM |

Figure 8:
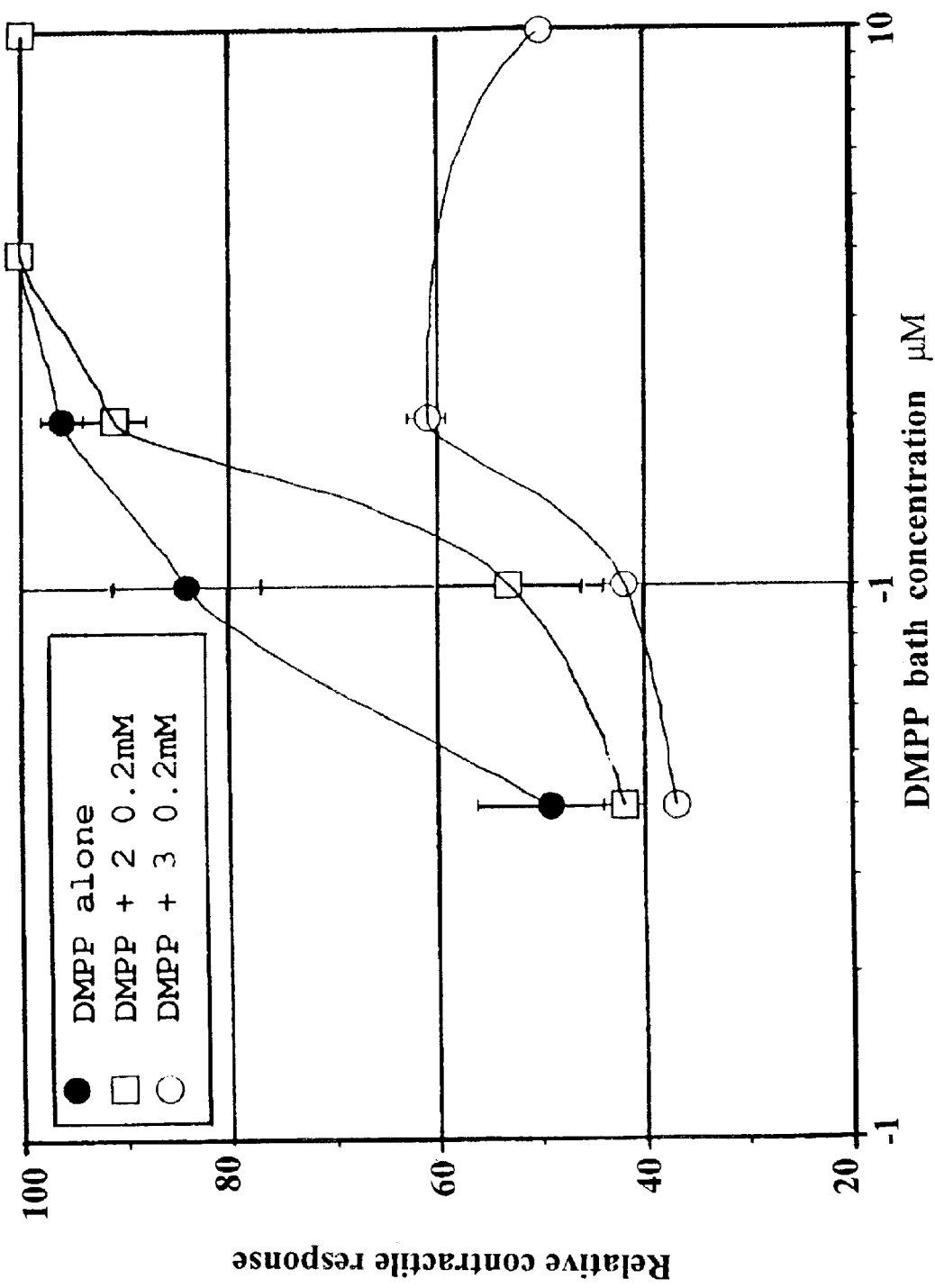
FIG. 8: Contractile response of the guinea-pig ileal preparation to rising concentrations of dimethyl-phenylpiperazimium chloride (DMPP) in the presence of 0.2 mM (R)-N-acetyl-1-aminoindan (2a) or N-acetyl-3-amino-1H-indene (3).

The results of contractile inhibitory activity of the present compounds in the DMPP system parallels the results of EXAMPLES 9 and 10, i.e., compounds 6, 5, 3 being more potent in reverse order, with 5 and 6 being close in activity. In the other procedure, while rising concentrations of DMPP can overcome the depression caused by compound 2a at 200 uM, thus reversing its effect almost to full restoration of the response to DMPP, the effect of compound 3 at 200 uM is not reversible by rising concentrations of DMPP. This is shown in FIG. 8, with the understanding that lower bath concentrations of compound 3 (not shown) have a similar effect, progressively lowering the maximal response to DMPP. Thus, the effect of 3 in blocking post-ganglionic nerve stimulus is of the irreversible type. This finding constitutes an unexpected but fundamental distinction between compounds 3 and the related 2a.

Example 12

Potentiation of the Inhibitory Effect of Adenosine on Neurotransmitter Release

Experimental Protocol

The test system used is the intramural electrically-stimulated guinea-pig ileal preparation as described in EXAMPLE 10. Adenosine added to the organ bath in rising concentrations in the range 0.1–10 uM causes a dose-dependent decrease in contraction amplitude, with an EC50 of about 1 uM. Two different procedures were used in order to demonstrate potentiation of the adenosine effect by the test compounds.

In procedure I, the effect of a given concentration of adenosine, usually, 0.2 or 0.4 uM was first determined and related to the full contractile response in the absence of adenosine. After washout and restoration of the full response, a given dose of the test compound was added to give a bath concentration in the range of 20–400 uM. The amplitude of the contractile response was recorded. Now, adenosine was added at the same dose initially used, and the effect of adenosine in the presence of the test compound was recorded.

In case of potentiation of adenosine by the test compound, the combined effect found must significantly exceed the calculated effect of the two agents when applied separately. The calculated effect is the product of the responses to each of the two agents when applied separately. The potentiation ratio is defined as (100%found)/(100-% calculated).

Results

The potentiation ratios of the depressant action of adenosine in the presence of the test compounds are given in Table 5.

TABLE 5

Potentiation of adenosine depression of contractile response to electric nerve stimulation of the guinea-pig ileal preparation in the presence of 3-amino-1H-indenes

| Adenosine uM | Drug, conc. range (uM) | Mean potentiation ratio ± SEM | Min | Max |
|---|---|---|---|---|
| 0.4 | 3, 20–400 | 1.49 ± 0.075 | 1.29 | 1.74 |
| 0.4 | 5, 50–200 | 2.19 ± 0.36 | 1.47 | 2.60 |
| 0.4 | 6, 25–50 | 1.93 ± 0.39 | 1.54 | 2.32 |
| 0.2 | 2a, 40–400 | 1.31 ± 0.05 | 1.19 | 1.43 |
| 0.1 | 2, 40–400 | 1.35 ± 0.07 | 1.16 | 1.49 |
| 0.2 | 2, 40–400 | 1.24 ± 0.16 | 0.79 | 1.51 |

SEM = standard error of the mean

Table 5 shows that the potentiation ratio for a given member is almost constant throughout a wide range of concentration of the potentiating agent. In all cases, the difference between the calculated and observed response was statistically significant. Compounds 6, 5 and 3 were more potent than compound 2 which was more potent than compound 2a. While compound 5 is shown to be slightly more potent than compound 6 in this EXAMPLE, the result is consistent however with the results of EXAMPLES 10 and 11 which showed that compounds 6 and 5 are more potent over compound 3 and that compounds 5 and 6 are closer in their potencies. In procedure II, the dose response to adenosine was determined before and after exposure of the preparation to the test drug and washout of the test drug from the organ bath. In this case, significant potentiation of adenosine was observed even though the test drug had been washed out from the organ bath. In fact, the potentiation ratio, as defined earlier, was even higher than found in the presence of the test compounds (Procedure I), reaching very high values. The data is given in Table 6.

TABLE 6

Potentiation of the depression caused by adenosine of the contractile response to electric nerve stimulation of the guinea-pig ileal preparation after exposure to and washout of 3-amino-1H-indenes

| Adenosine uM | Drug, conc. range (uM) | Mean potentiation ratio ± SEM | Min | Max |
|---|---|---|---|---|
| 0.4 | 3, 100–400 | 1.54 ± 0.25 | 1.14 | 1.99 |
| 0.4 | 5, 50–400 | 5.55 ± 1.0 | 3.78 | 7.28 |
| 0.4 | 6, 50–400 | 8.82 ± 1.2 | 6.86 | 12.28 |
| 0.4 | 2a, 1000 | 1.41 | | |
| 0.4 | 2, 1000 | 0.87 | | |

Table 6 shows that except in the case of 2, the differences between the response to adenosine before and after exposure and washout of the test compounds was statistically significant. The potentiation effect persisted 10–15 minutes after washout. The original response to adenosine could be restored at a rate depending on the nature of the potentiating agent applied. It was the fastest in the case of compound 2a, and the slowest in the case of compounds 6.

It is noteworthy that repeated exposure of the preparation to adenosine alone in cycles 10–15 minutes apart did not cause self-potentiation to adenosine. This persistent potentiating effect of the presently disclosed compounds after their washout from the organ bath is unexpected and is a unique and surprising result.

Discussion

A. Synthesis of Compounds

All the compounds of 1 were prepared from the corresponding oximes 9. Indenamide (3) was obtained from this ($R^2$=H, n=1) by reductive acetylation according to the method of D. H. R. Barton (R. B. Boar et al., J. Chem. Soc., Perkin Trans. I, 1975, 1237–41). Indenamide (3) was prepared in superior yield by reductive acetylation with acetic anhydride/titanium triacetate (Boar, loc. cit., D. H. R. Barton et al., Tetrahedron Letters (1988) 29 3343–6), which method was also used for compounds 4 and 6. With formic acetic anhydride the formenamides 5 and 7 were obtained. Acyl homologues of 3 can similarly be obtained by using the anhydrides of lower alkanoic acids such as commercially available propionic or butyric anhydrides.

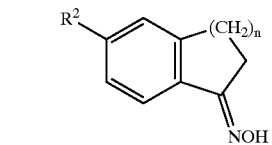

9

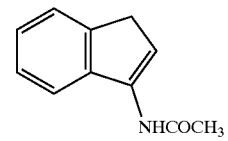

3

4

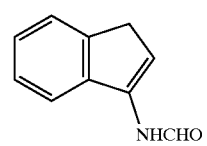

5

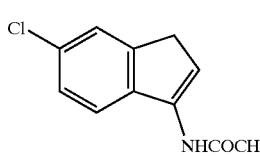

6

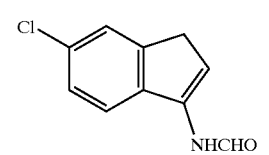

7

Though more accessible than titanium triacetate, iron powder in acetic anhydride (D. H. R. Barton and S. Z. Zard, J. Chem. Soc., Perkin Trans. I, 1985, 2191–2; N. M. Laso et al., Tetrahedron Letters (1996) 37 1605–8) gave a discolored sample of compound 3 in poor yield. The titanium triacetate method is thus preferred for compound 3 and its analogs.

Compound 3 was also obtained in good yield, but discolored, by the method of Ruschig et al., (H. Ruschig et al., Chem. Ber., (1955) 88 83–94). In this method 1-indanamine 10 was oxidized via N-chlorination and elimination to the imine 11, which was acylated with an anhydride. The reagents for this method are more accessible than titanium triacetate, but, for compound 3, the latter method is preferred.

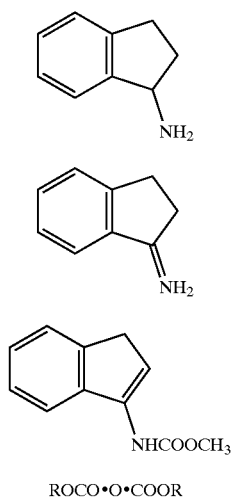

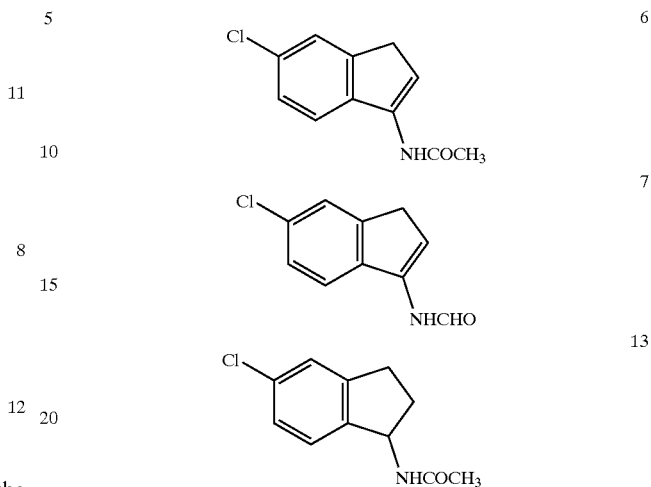

However, the method of Ruschig was used to obtain the N-methoxycarbonyl-3-amino-1H-indene (8), using dimethyl pyrocarbonate (12, R=Me) as the anhydride. Other alkoxy homologues of 8 can be obtained by acylating with the corresponding dialkyl pyrocarbonate such as commercially available diethyl pyrocarbonate (12, R=Et).

While the above discussion uses specific examples to illustrate the present invention, its scope is not necessarily limited to those ilustrations only.

B. Pharmacological Experiments

The utility of the compounds of this invention to treat afflictions of the central nervous system is shown by experiments of behavioral activity in mice and biochemical activity in guinea pig ileal preparations.

1) Protection Against Hypobaric Hypoxia in Mice

The hypobaric hypoxia test in mice is considered a preliminary screening test for potential neuroprotective agents, irrespective of the mechanism of action (see, for example, M. Nakanishi et al., Protective effect of antianxiety drugs against hypoxia, Life Science 13, 467–474, 1973; Y. Oshiro et al., Novel cerebroprotective agents with central nervous system stimulating activity. Synthesis and pharmacology of the 1-(acylamino)-7-hydroxyindan derivatives. J. Med. Chem. 34, 2014–2023, 1991). Mice exposed to an atmospheric pressure of 200 mm Hg can only survive a maximum of about 150 seconds. Survival time is extended many folds when the mice have been treated with a potential neuroprotective agent. Hence, the relative increase in survival time is an indication of neuroprotective potency.

The presently disclosed novel compounds 3, 5, 7, 6 and 8 showed strong activity in this model (in decreasing order of activity) at a dose of 25 mg/kg. For example, compound 3 showed strong dose-dependent protection of mice against the condition of hypobaric hypoxia, affording 1000% protection over 2a (control) at 50 mg/kg with minor and transient side effects such as slight sedation, hypopnea and defecation.

Neuroprotectant potency is known to be influenced by configuration because the R-enantiomer 2a of N-acetyl-1-aminoindan showed greater activity than the S-enantiomer. The enhanced activity of the above achiral compounds relative to (R)-N-acetyl-1-aminoindan 2a and its enantiomer is therefore surprising. In the same way the chloroindenamides 6 and 7 are much more active in this test than the corresponding chloroindanamide 13. The tetralin derivative 4 was inactive in this model.

This unexpected activity however makes the presently disclosed compounds useful in treating conditions of neurodegeneration such as Alzheimer's disease.

2) Protection Against Electroshock-induced Seizure in Mice

Protection of mice against seizures induced by electroshock is a widely used model to probe for potential anti-epileptic agents (see, for example, Y. I. Sohn et al., Anticonvulsant properties of diphenylthiohydantoin, Arch. Int. Pharmacodyn. 188, 284–289, 1970).

Compounds 3, 4, 5, and 6 were all more potent than sodium valproate, a known and potent anti-epileptic drug but all were less potent than 2a, except for compound 6 whose potency was within the range of 2a. This result is surprising. Even though compound 6 has the same range of anticonvulsant potency as that of 2a, it is a superior neuroprotectant in the hypobaric hypoxia test at low doses, indicating that perhaps compound 6 has a different mechanism of action from compound 2a.

3) Decrease of Response to Electrical Stimulation in Guinea-pig Ileal Preparation Blocking or decreasing neural excitability evoked by programmed electric stimulation is another indicator of a compound's potential neuroprotective activity. A convenient test system uses the guinea-pig ileal preparation mounted in an organ bath (see, for example, Eiichi Hayashi et al., European J. Pharmacol 48, 297–307, 1978).

It is generally known that decreased response to electrical stimulation in this model is sensitive to molecular conformation because the R-enantiomer 2a is more active than its S-enantiomer. Surprisingly however, compound 3 was considerably more effective than compound 2a in decreasing the contractile response to electrically-induced nerve stimulation. The superior potency of compound 3 was unexpected because it is achiral and rather planar compared to 2a. The formyl analogue 5 and the chloro-derivative 6 also showed greater potency than 2a. On the other hand, the tetralin derivative 4 was of comparable potency to compound 2a.

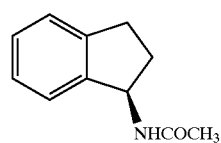

2a

-continued

3

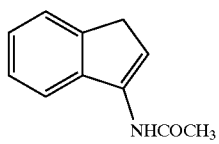

6

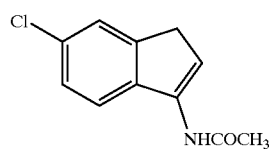

4) Decrease in Response of Nerve Stimulation Evoked by a Nicotinic Agonist

When intramural nerve stimulation occurs, as in the case of electrical stimulation, the contractile effector substance is released from nerve endings by a depolarization wave that propagates along the parasympathetic nerve fiber until its junction with smooth muscle of the ileum. An alternative but not equivalent procedure is stimulation of parasympathetic ganglia by an appropriate nicotinic agonist such as 1-N,N-dimethyl-4-N-phenylpiperazinium chloride (DMPP). Stimulation of parasympathetic ganglia causes a depolarization wave in the post-ganglionic nerve fiber which terminates on the smooth muscle of the ileum, causing release of contractile effector and contraction (see, for example, E. S. Vizi, Acetylcholine release from guinea-pig ileum by parasympathetic ganglion stimulants and gastrin-like polypeptides, Br. J. Pharmacol. 47, 765–77. 1973).

Guinea pig ileal preparation was used to measure the decrease of response to nerve stimulation evoked by DMPP. Compounds 3, 5 and 6 all were more effective than 2a in depressing the stimulation by DMPP. It is generally known that compound 2a is a reversible blocker of post-ganglionic nerve stimulation. Surprisingly however, compound 3 irreversibly blocked post-ganglionic nerve stimulation, indicating that its inhibition differs in some fundamental aspect from that of compound 2a. This surprisingly prolonged inhibition can be exploited to provide neuroprotection against neural injury in cases of stroke or trauma.

5) Potentiation of the Inhibitory Effect of Adenosine on Neurotransmitter Release Endogenous adenosine, released following neural injury as in stroke or trauma, is neuroprotective. It causes a decrease in neuronal excitability following hyperpolarization and a decrease in excessive excitatory neurotransmitter release, especially glutamate (see, for example, K. A. Rudolphi et al., Neuroprotective role of adenosine in cerebral ischemia, Trends in Pharmacol. Sci. 13, 439–445, 1992).

However, the effect of endogenous adenosine is limited in time and scope, partly because endogenous supplies are limited in quantity and partly because adenosine has an extremely short half-life in extracellular fluid. Various procedures were offered to redress this shortcoming, such as the use of drugs that inhibit the cellular uptake of adenosine, e.g. dipyridamol, or that inhibit its further metabolism either into inosine or its 5'-monophosphate (see, for example, E. Hayashi et al., The development of tachyphylaxis to electrical stimulation in guinea-pig ileal longitudinal muscles and the possible participation of adenosine and adenine nucleotides, Br. J. Pharmacol. 63, 457–64, 1978).

The compounds of the present invention are effective exogenous adenosine potentiators. Compounds 5 and 6 are more effective than 3 and all three are more effective than the N-acetyl-1-aminoindan 2. This result is consistent with the result from above described pharmacologic studies of this application.

However, test compounds 5 and 6 exhibited surprisingly prolonged potentiating effect, which effect was retained by guinea pig ileal preparation after wash-out from the organ bath. This unique and unexpected property of irreversible or prolonged inhibition can be especially useful to provide neuroprotection against neural injury in cases of stroke or trauma.

We claim:

1. A pharmaceutical composition comprising a compound having the structure:

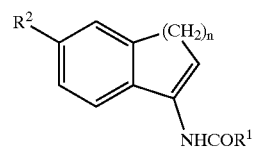

wherein n is 1 or 2, $R^1$ is hydrogen, a linear or branched chain $C_1$–$C_8$ alkyl or a linear or branched chain $C_1$–$C_8$ alkoxy and $R^2$ is hydrogen or a halogen and a pharmaceutically acceptable carrier selected for a particular route of administration, the administration being selected from the group consisting of oral, intravenous, intraperitoneal, intramuscular, subcutaneous, intra-articular, intra-nasal, intra-thecal, intra-dermal, transdermal and inhalation.

2. The pharmaceutical composition of claim 1, wherein the halogen is chlorine.

3. A compound having the structure:

wherein n is 1 or 2, $R^1$ is hydrogen, a linear or branched chain $C_1$–$C_8$ alkyl or a linear or branched chain $C_1$–$C_8$ alkoxy and $R^2$ is hydrogen or a halogen; provided that when n is 1 and $R^1$ is isobutyl, $R^2$ cannot be H, and that when n is 2, $R^1$ and $R^2$ both cannot be hydrogen.

4. The compound of claim 3, wherein the halogen is chlorine.

5. The compound of claim 3 selected from the group consisting of:

N-formyl-3-amino-1H-indene;
N-acetyl-3-amino-6-chloro-1H-indene;
N-formyl-6-chloro-3-amino-1H-indene; and
N-methoxycarbonyl-3-amino-1H-indene.

6. The compound of 3 claim having the structure:

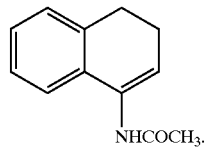

7. A method of treating a subject suffering from a disorder selected from the group consisting of Alzheimer's disease, head trauma, stroke, hypoxia, anoxia, epilepsy, convulsions, or seizures which comprises administering to the subject an amount of the pharmaceutical composition of claim 1 effective to treat the disorder in the subject.

8. The method of claim 7, wherein the disorder is Alzheimer's disease.

9. The method of claim 7, wherein the disorder is head trauma.

10. The method of claim 7, wherein the disorder is stroke.

11. The method of claim 7, wherein the disorder is hypoxia.

12. The method of claim 7, wherein the disorder is anoxia.

13. The method of claim 7, wherein the disorder is epilepsy.

14. The method of claim 7, wherein the disorder is convulsions.

15. The method of claim 7, wherein the disorder is seizures.

16. The method of claim 7, wherein the administering comprises oral, parenteral, topical, transdermal, rectal, nasal, or buccal administration.

17. A compound having the structure:

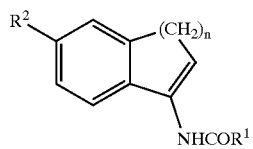

wherein n is 1 or 2, $R^1$ is hydrogen, a linear or branched chain $C_1$–$C_8$ alkyl or a linear or branched chain $C_1$–$C_8$ alkoxy and $R^2$ is hydrogen or a halogen; provided that when n is 1 and $R^1$ is isobutyl, $R^2$ cannot be H, that when n is 2, $R^1$ and $R^2$ both cannot be hydrogen, and that when $R^1$ is a methyl group, $R^2$ cannot be hydrogen.

18. The compound of claim 17 selected from the group consisting of:

N-formyl-3-amino-1H-indene;
N-acetyl-3-amino-6-chloro-1H-indene;
N-formyl-6-chloro-3-amino-1H-indene; and
N-methoxycarbonyl-3-amino-1H-indene.

19. The compound of claim 17 having the structure:

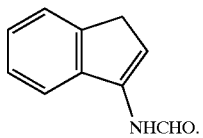

20. The compound of claim 17 having the structure:

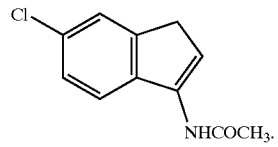

21. The compound of claim 17 having the structure:

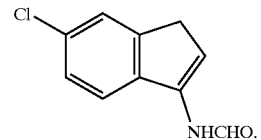

22. The compound of claim 16 having the structure:

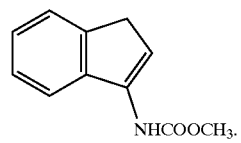

23. A pharmaceutical composition comprising a therapeutically effective amount of the compound of claim 3 and a pharmaceutically acceptable carrier.

24. A pharmaceutical composition comprising a therapeutically effective amount of the compound of claim 4 and a pharmaceutically acceptable carrier.

25. A pharmaceutical composition comprising a therapeutically effective amount of the compound of claim 5 and a pharmaceutically acceptable carrier.

26. A pharmaceutical composition comprising a therapeutically effective amount of the compound of claim 6 and a pharmaceutically acceptable carrier.

27. A pharmaceutical composition comprising a therapeutically effective amount of the compound of claim 17 and a pharmaceutically acceptable carrier.

28. A pharmaceutical composition comprising a therapeutically effective amount of the compound of claim 18 and a pharmaceutically acceptable carrier.

29. A pharmaceutical composition comprising a therapeutically effective amount of the compound of claim 19 and a pharmaceutically acceptable carrier.

30. A pharmaceutical composition comprising a therapeutically effective amount of the compound of claim 20 and a pharmaceutically acceptable carrier.

31. A pharmaceutical composition comprising a therapeutically effective amount of the compound of claim 21 and a pharmaceutically acceptable carrier.

32. A pharmaceutical composition comprising a therapeutically effective amount of the compound of claim 22 and a pharmaceutically acceptable carrier.

33. The method of claim 7, wherein the amount is an amount from about 12.5 mg/kg to about 150 mg/kg.

34. The compound of claim 3 having the structure:

35. A pharmaceutical composition comprising a therapeutically effective amount of the compound of claim 34 and a pharmaceutically acceptable carrier.

* * * * *